US012391910B2

(12) United States Patent
Koseki et al.

(10) Patent No.: US 12,391,910 B2
(45) Date of Patent: Aug. 19, 2025

(54) SPHERE CULTURE MEMBER, CULTURE CONTAINER, METHOD FOR PROCESSING PERFORATED MEMBER, AND CLEANING CONTAINER

(71) Applicant: TOYO SEIKAN GROUP HOLDINGS, LTD., Tokyo (JP)

(72) Inventors: Osamu Koseki, Kanagawa (JP); Satoshi Tanaka, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 963 days.

(21) Appl. No.: 17/233,709

(22) Filed: Apr. 19, 2021

(65) Prior Publication Data

US 2021/0238525 A1    Aug. 5, 2021

Related U.S. Application Data

(63) Continuation of application No. PCT/JP2019/040804, filed on Oct. 17, 2019.

(30) Foreign Application Priority Data

Oct. 20, 2018  (JP) .................. 2018-198005

(51) Int. Cl.
  *C12M 1/12*    (2006.01)
  *B29C 43/02*    (2006.01)
  *C12M 1/00*    (2006.01)

(52) U.S. Cl.
  CPC .......... *C12M 25/00* (2013.01); *B29C 43/021* (2013.01); *C12M 23/26* (2013.01); *C12M 23/34* (2013.01); *C12M 39/00* (2013.01)

(58) Field of Classification Search
  CPC ...... C12M 25/00; C12M 23/26; C12M 23/14; C12M 23/34
  See application file for complete search history.

(56) References Cited

U.S. PATENT DOCUMENTS

7,964,392 B2    6/2011  Hatano et al.
10,760,041 B2 *  9/2020  Liderfelt ............... C12M 29/04
          (Continued)

FOREIGN PATENT DOCUMENTS

CN    1942575 A    4/2007
JP   2010-063379 A    3/2010
          (Continued)

OTHER PUBLICATIONS

Office Action issued in Chinese Patent Application No. 2019-80067981.2, mailed on Aug. 24, 2023, with English Translation of Substantial Part (13 pages).
          (Continued)

*Primary Examiner* — Holly Kipouros
(74) *Attorney, Agent, or Firm* — Nakanishi IP Associates, LLC

(57) ABSTRACT

It is possible to efficiently replace a medium, clean spheres, and arrange spheres at regular intervals in the formation of spheres. A member is capable of capturing spheres, the member having a first surface and a second surface on an opposite side of the first surface, and having a plurality of recesses; the recess having an opening formed in the first surface, and one microhole being formed for each opening in the second surface; a circle or inscribed circle of the opening having a diameter a of 50 μm or more and 1 mm or less, a circle or inscribed circle of the microhole having a diameter b of 1 μm or more and less than 200 μm, and a and b satisfying a>b.

4 Claims, 18 Drawing Sheets

(56) References Cited

U.S. PATENT DOCUMENTS

| | | |
|---|---|---|
| 2008/0274536 A1 | 11/2008 | Hatano et al. |
| 2014/0322747 A1 | 10/2014 | Ito |
| 2016/0304821 A1 | 10/2016 | Ito |
| 2016/0312164 A1 | 10/2016 | Ito |
| 2017/0015966 A1 | 1/2017 | Sumi |
| 2017/0159002 A1 | 6/2017 | Ito |
| 2017/0342363 A1 | 11/2017 | Fang et al. |
| 2018/0201892 A1* | 7/2018 | Gomi ............... G02B 21/14 |
| 2019/0002834 A1 | 1/2019 | Tanabe et al. |
| 2019/0127677 A1 | 5/2019 | Tanaka et al. |
| 2019/0322969 A1 | 10/2019 | Fang et al. |
| 2021/0222103 A1* | 7/2021 | Martin ............... C12M 23/20 |

FOREIGN PATENT DOCUMENTS

| | | |
|---|---|---|
| JP | 2017-536817 A | 12/2017 |
| WO | 2007022026 A2 | 2/2007 |
| WO | 2013/093954 A1 | 6/2013 |
| WO | 2015/087369 A1 | 6/2015 |
| WO | 2015/129263 A1 | 9/2015 |
| WO | 2016/020992 A1 | 2/2016 |
| WO | WO-2016020988 A1 * | 2/2016 ............ C12M 23/12 |
| WO | 2017/110004 A1 | 6/2017 |
| WO | 2017/115865 A1 | 7/2017 |
| WO | 2017/183570 A1 | 10/2017 |
| WO | WO-2018057769 A1 * | 3/2018 ............ C12M 23/08 |

OTHER PUBLICATIONS

International Search Report issued in PCT/JP2019/040804 mailed on Dec. 24, 2019 with English Translation (5 bages).

Extended European Search Report issued in European Patent Application No. 19872387.6, dated Jun. 20, 2022 (10 pages).

Office Action issued in Japanese Patent Application No. 2018-198005, mailed on Sep. 6, 2022, with English Translation (12 pages).

* cited by examiner (A)

(B)

(C)

SPHERE CULTURE MEMBER, CULTURE CONTAINER, METHOD FOR PROCESSING PERFORATED MEMBER, AND CLEANING CONTAINER

TECHNICAL FIELD

The present invention relates to a cell culture technique, in particular, relates to a technique of promoting the efficiency of sphere formation.

BACKGROUND ART

In recent years, large amounts of adherent cells, such as stem cells including iPS cells and ES cells, are cultured not only by attaching cells to a culture container to grow, but also by using a method of culturing cells in a three-dimensional state closer to in vivo by forming spheres (spheroids, aggregates) using a culture container, such as a microwell plate, coated with a material having low adhesion to cells.

Specifically, a step of forming spheres, a step of culturing cells to grow while maintaining the sphere state, and a step of inducing the differentiation of cells in the sphere state are performed.

In addition, there are a method of attaching and growing iPS cells etc. in a culture container, inducing differentiation in the attached state, and using a microwell plate to form spheres from the obtained differentiated cells; and a method of inducing the differentiation of cells in the attached state, then once cryopreserving the differentiated cells, thawing them again, and then forming spheres. Thus, operations are performed in the sphere state in various steps.

Further, after the formation of spheres and before the administration of the spheres that have been induced to differentiate into target cells to the living body, they may be washed with a phosphate buffer or physiological saline, or may be suspended in water for injection or the like.

Here, when forming spheres using a culture container, such as a microwell plate, there was a problem that air bubbles remained in each well when the medium was dropped into the microwell plate. That is, the air bubbles remaining in the wells would inhibit the formation of spheres; however, it was extremely difficult to remove all of the air bubbles from the wells.

Moreover, when culturing spheres using a microwell plate or inducing the differentiation of spheres into a specific tissue, it is generally required to replace the entire medium in the culture container. However, with a method using such a microwell plate, it was extremely difficult to replace the medium accumulated in the recesses of the wells while capturing the spheres in the recesses.

Furthermore, when actually using spheres formed by a microwell plate or the like for treatment, it is necessary to collect the spheres in a different container; however, before this operation, it is necessary to remove the medium and single cells attached to the spheres by cleaning the spheres.

Examples of the method of collecting and cleaning spheres include a method using a container having a mesh member. In this method, spheres formed in a microwell plate were suspended in a medium by pipette operation or the like and collected, then the spheres suspended in the medium were dropped into the container having a mesh member to discharge the medium, and the medium was further rinsed with physiological saline or the like to clean the spheres.

With such a method, single cells that did not form spheres could be removed from the mesh, or the medium could be discharged; however, the spheres came into contact with each other to overlap and further aggregated, which caused a problem that it was difficult to obtain spheres with a desired size.

CITATION LIST

Patent Literature

Patent Document 1: JP-A-2017-536817
Patent Document 2: WO 2015/129263 pamphlet

SUMMARY OF INVENTION

Technical Problem

Therefore, in order to replace the medium accumulated in the recesses, it is conceivable to form holes in the bottom surface of the recesses. An example of the prior art related to a culture container including recesses with holes is the cell culture insert disclosed in Patent Document 1.

This cell culture insert includes a first open end and a second end having an opening, and a porous membrane disposed on the opening of the second end. It is considered that the medium can be easily replaced by using such a cell culture insert.

However, since the porous membrane was disposed on the opening, this cell culture insert was neither capable of suitably discharging single cells, nor suitable for the mass culture of spheres.

Another example of the prior art related to a culture container including recesses with holes is the spheroid-producing device disclosed in Patent Document 2.

This spheroid-producing device has a plurality of holes penetrating between a first surface and a second surface, and is capable of mass-producing uniform spheroids.

However, this spheroid-producing device uses the so-called hanging-drop method to culture spheroids by popping them out of the holes in the bottom surface due to the surface tension of the medium, and the opening on the second surface is larger than the size of spheroids. Therefore, this culture container was not applicable to replace the medium accumulated in the recesses while capturing the spheroids in the recesses.

The present invention was made in view of the above circumstances. An object of the present invention is to provide a sphere culture member, a culture container, a method for processing a perforated member, and a cleaning container, all of which allow, for example, efficient medium replacement, cleaning of spheres, and arrangement of spheres at regular intervals in the formation of spheres.

Solutions to Problem

In order to achieve the above object, a sphere culture member of the present invention is a member capable of capturing spheres, the member having a first surface and a second surface on an opposite side of the first surface, and having a plurality of recesses; the recess having an opening formed in the first surface, and one microhole being formed for each opening in the second surface; a circle or inscribed circle of the opening having a diameter a of 50 μm or more and 1 mm or less, a circle or inscribed circle of the microhole having a diameter b of 1 μm or more and less than 200 μm, and a and b satisfying a>b.

Further, a culture container of the present invention includes the first surface and the recess-forming surface of the sphere culture member described above as a culture surface.

Moreover, a method for processing a perforated member according to the present invention is a method for processing a perforated member to make a plurality of holes in the member using a mold. The member is a film having a first surface and a second surface on an opposite side of the first surface. The hole is a recess having an opening in the first surface and one microhole for each opening in the second surface. In a two-dimensional model of the recesses viewed from a side surface, the mold and the film satisfy a formula: $t = a \times h/2(a+b)$, wherein t is a thickness of the film, h is a height of a projection in the mold corresponding to the recess, b is a width of a tip of the projection in the mold corresponding to the microhole of the recess, and a is a width between the tips of the adjacent projections in the mold. The mold is pressed against the film to form the microholes in the film using the mold and the film.

In addition, a cleaning container of the present invention includes the sphere culture member described above.

Advantageous Effects of Invention

According to the present invention, it is possible to provide a sphere culture member, a culture container, a method for processing a perforated member, and a cleaning container, all of which allow, for example, efficient medium replacement, cleaning of spheres, and arrangement of spheres at regular intervals in the formation of spheres.

DESCRIPTION OF EMBODIMENTS

Hereinafter, embodiments of the sphere culture member, the culture container, the method for processing a perforated member, and the cleaning container according to the present invention will be described in detail. Note that the present invention is not limited to the specific contents of the following embodiments and examples.

[Sphere Culture Member]

Figure 1:
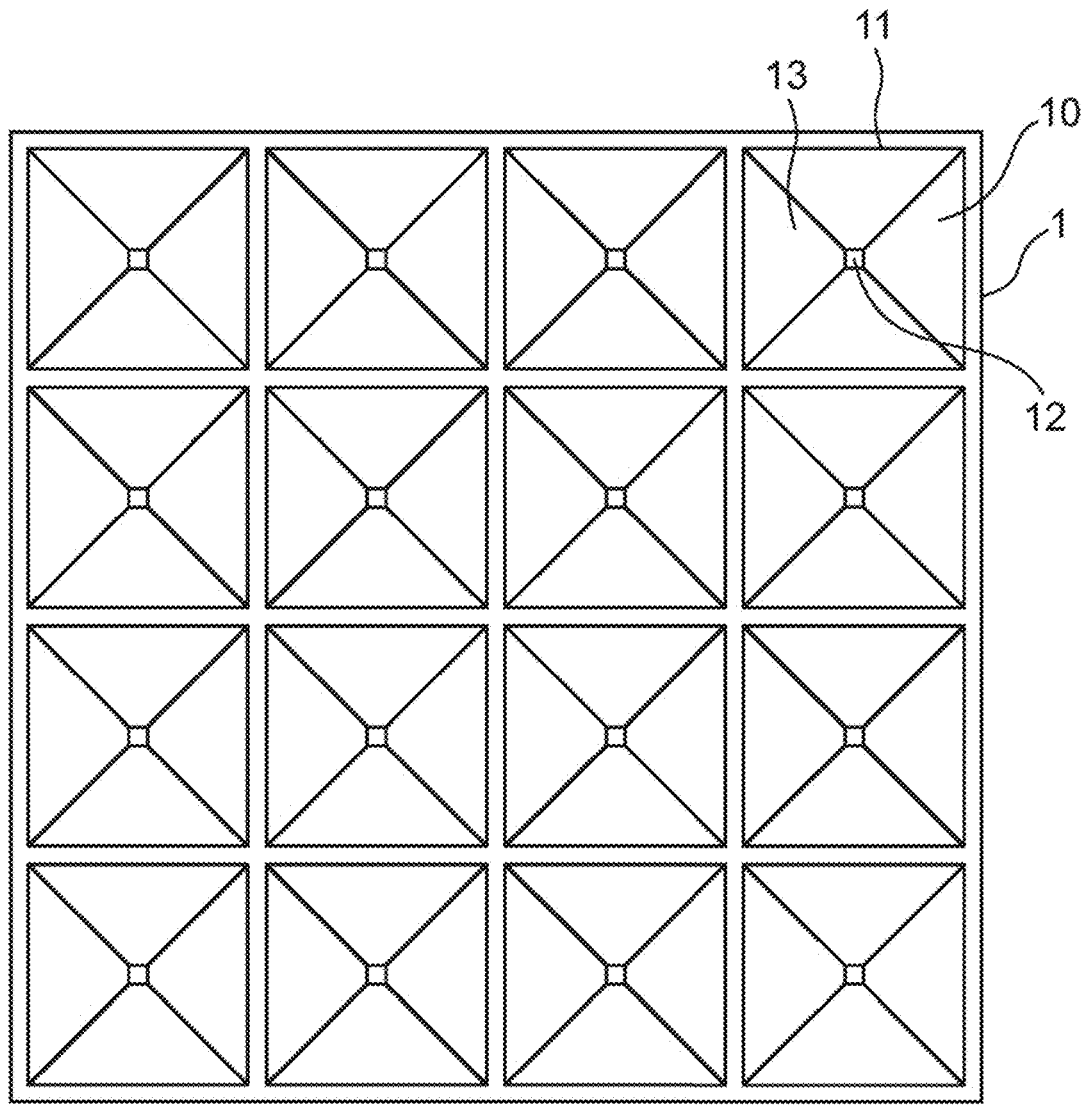
FIG. 1 is a schematic diagram illustrating the structure of a sphere culture member according to an embodiment of the present invention.
Figure 1:
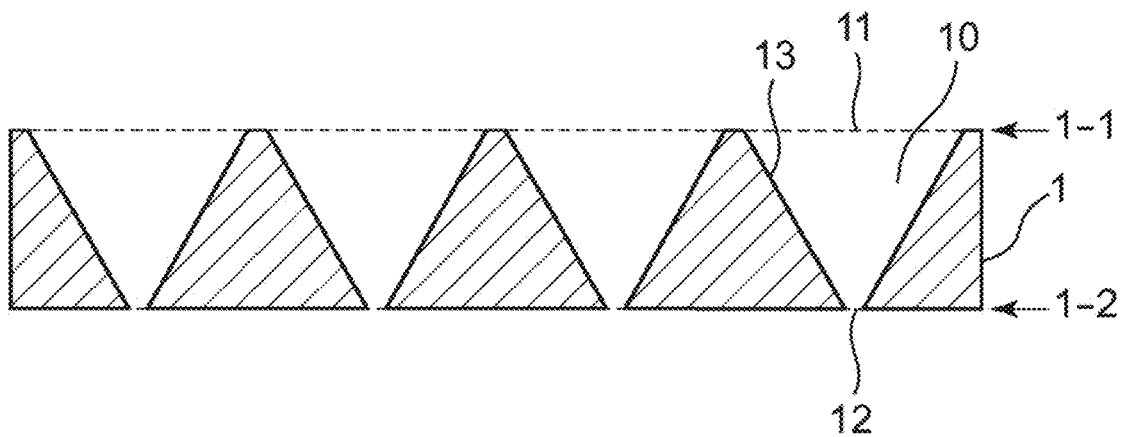
Figure 2:
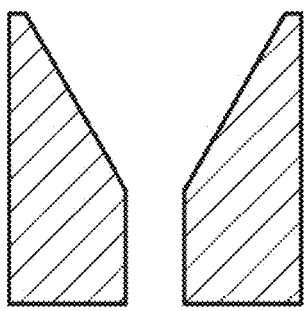
FIG. 2 is an explanatory diagram of microholes not suitable or suitable for the sphere culture member according to the embodiment of the present invention.
Figure 2:
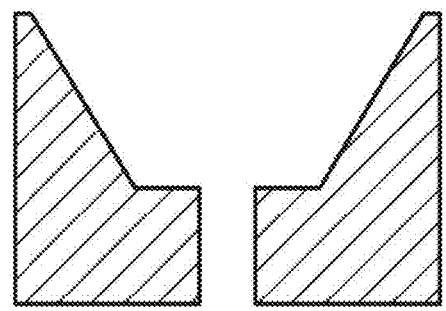
Figure 2:
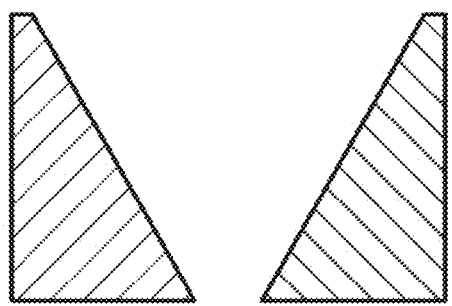
Figure 3:
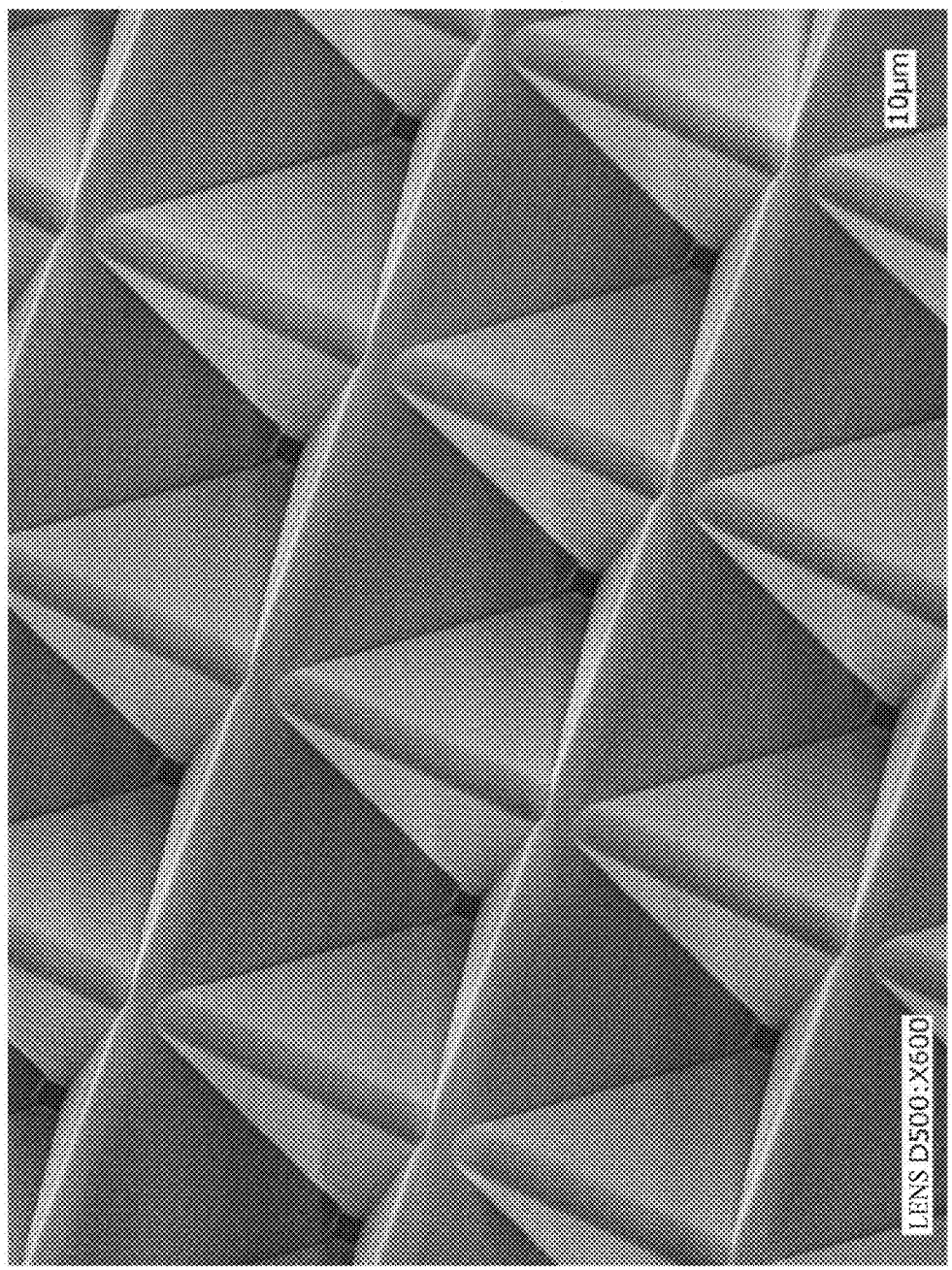
FIG. 3 is a micrograph obtained by photographing a sphere culture member of an example.

First, a sphere culture member according to an embodiment of the present invention will be described with reference to FIGS. 1 to 3. FIG. 1 is a schematic diagram illustrating the structure of the sphere culture member of the present embodiment, and shows a plan view and a front view of a part of the sphere culture member. FIG. 2 is an explanatory diagram of microholes not suitable or suitable for the sphere culture member according to the present embodiment. FIG. 3 is a micrograph obtained by photographing a sphere culture member prepared in an example, described later.

The sphere culture member according to the embodiment of the present invention has a plurality of recesses, and sections including the recesses each accommodate one sphere.

Further, the sphere culture member of the present embodiment has one microhole in the bottom surface of each recess, which make it possible to remove unnecessary objects, such as unnecessary cells (e.g., dead cells) that cannot function as spheres, through the microholes from the recesses while capturing spheres.

Specifically, as shown in FIG. 1, the sphere culture member 1 of the present embodiment has a first surface 1-1 and a second surface 1-2 on the opposite side of the first surface 1-1, openings 11 of recesses 10 are formed in the first surface 1-1, and one microhole 12 is formed for each opening 11 in the second surface 1-2.

Further, in the sphere culture member 1 of the present embodiment, it is preferable that a circle or inscribed circle of each opening 11 has a diameter a of 50 μm or more and 1 mm or less, that a circle or inscribed circle of each microhole 12 has a diameter b of 1 μm or more and less than 200 μm, and that a and b satisfy a>b.

The openings 11 and the microholes 12 have a circular or polygonal shape in some cases. Therefore, the diameters of these include the diameter of an inscribed circle of a polygon, in addition to that of a circle.

Here, the size of single cells is about 6 μm to 15 μm, and many of them have a size of about 10 μm. One sphere can be formed by aggregation of about 300 to several thousands of single cells. The size of the thus-formed spheres is about 50 μm to 100 μm for small spheres, and about 200 μm to 300 μm for large spheres.

Accordingly, in order to be able to form spheres in the recesses 10 of the sphere culture member 1 of the present embodiment and take out them, the diameter a of the circle or inscribed circle of the opening 11 is preferably set to 50 μm or more and 1 mm or less, as described above.

Further, depending on the size of the target spheres, the diameter a of the circle or inscribed circle of the opening 11 can be set in various ways within the above range.

For example, the lower limit of the diameter a of the circle or inscribed circle of the opening 11 may be 60 μm or more, 70 μm or more, 80 μm or more, 90 μm or more, 100 μm or more, 110 μm or more, 120 μm or more, 150 μm or more, or the like. Further, the upper limit of the diameter a of the circle or inscribed circle of the opening 11 may be 1 mm or less, 900 μm or less, 800 μm or less, 700 μm or less, 500 μm or less, or the like.

In order to be able to suitably remove single cells, dead cells, debris, etc., from the recesses 10 of the sphere culture member 1 of the present embodiment, the diameter b of the circle or inscribed circle of the microhole 12 is preferably set to 1 μm or more and less than 200 μm, as described above.

Moreover, from such a viewpoint, the diameter b of the circle or inscribed circle of the microhole 12 can be set in various ways within the above range.

For example, the lower limit of the diameter b of the circle or inscribed circle of the microhole 12 may be 3 μm or more, 6 μm or more, 10 μm or more, 14 μm or more, 18 μm or more, or the like. Further, the upper limit of the diameter b of the circle or inscribed circle of the microhole 12 may be less than 200 μm, less than 180 m, less than 160 μm, less than 140 μm, less than 120 μm, less than 100 μm, less than 80 μm, less than 60 μm, less than 40 μm, or less than 20 m.

In the sphere culture member 1 of the present embodiment, it is preferable that wall surfaces 13 of the recesses 10 are integrated with the second surface 1-2 in which the microholes 12 are formed.

Moreover, in the sphere culture member 1 of the present embodiment, it is preferable that the wall surface 13 of each recess 10 is inclined from the opening 11 toward the microhole 12.

That is, for example, as shown in FIGS. 2 (A) and (B), when the recess 10 includes a portion perpendicular to the culture surface from the opening toward the microhole, or a plane portion with respect to the culture surface, it is more likely that the single cells etc. are clogged in the recesses.

Therefore, in the sphere culture member 1 of the present embodiment, the wall surface 13 of each recess 10 is preferably inclined from the opening 11 toward the microhole 12, as shown in FIG. 2 (C).

Further, in the sphere culture member 1 of the present embodiment, it is preferable that the openings 11 and/or the microholes 12 are formed into a polygonal shape, as shown in FIG. 1. This is because since cells are almost sphere, if the microholes 12 are formed into a circular shape, the single cells may be clogged and be difficult to discharge. Another reason is that if the openings 11 are formed into a circular shape, it may be difficult to take out the spheres.

Moreover, if the openings 11 are formed into a circular shape, an unnecessary planer section (dead space) is formed between the plurality of openings 11 in the first surface 1-1 of the sphere culture member 1, which causes a problem that the single cells remain in the dead space.

Therefore, the openings 11 and/or the microholes 12 preferably have a polygonal shape, such as a quadrilateral, and particularly preferably a square.

The sphere culture member 1 of the present embodiment including recesses 10 having such square openings 11 and microholes 12 can be produced by forming a truncated square pyramid male mold from metal or ceramic, and pressing the mold against a resin.

In the sphere culture member 1 of the present embodiment, the width between the adjacent openings 11 is preferably 50 μm or less.

That is, if the width between the adjacent openings 11 is wide, a dead space is formed in the first surface 1-1 of the sphere culture member 1, as with the above case, which causes a problem that the single cells remain in the dead space.

From such a viewpoint, the width between the adjacent openings 11 is more preferably 40 μm or less, even more preferably 30 μm or less, still even more preferably m or less, further still even more preferably 10 μm or less, and further still even more preferably 5 μm or less.

As the material of the sphere culture member 1 of the present embodiment, polyolefin-based resins, such as polyethylene and polypropylene, can be suitably used.

Examples thereof include polyethylene, ethylene-α-olefin copolymers, ethylene-vinyl acetate copolymers, ionomers using ethylene-acrylic acid or methacrylic acid copolymers and metal ions, and the like. Other examples include polyolefins, styrene-based elastomers, polyester-based thermoplastic elastomers, silicone-based thermoplastic elastomers, silicone resins, and the like. Still other examples include silicone rubber, flexible polyvinyl chloride resins, polybutadiene resins, ethylene-vinyl acetate copolymers, chlorinated polyethylene resins, polyurethane-based thermoplastic elastomers, polyester-based thermoplastic elastomers, silicone-based thermoplastic elastomers, styrene-based elastomers (e.g., SBS (styrene-butadiene-styrene), SIS (styrene-isoprene-styrene), SEBS (styrene-ethylene-butylene-styrene), and SEPS (styrene-ethylene-propylene-styrene)), polyolefin resins, fluorine-based resins, and the like.

Moreover, the sphere culture member 1 of the present embodiment can be suitably used as a material of a culture container. Due to the use of the first surface 1-1 and the surface that forms the recesses 10 of the sphere culture member 1 as a culture surface, the spheres can be accommodated in the recesses 10.

Further, the first surface 1-1 and the recesses 10 of the sphere culture member 1 of the present embodiment are preferably subjected to low-adhesion surface coating so that the spheres and single cells do not adhere thereto. Specifically, it is preferable to apply a cell adhesion inhibitor (cell adhesion-reducing agent).

Usable examples of cell adhesion inhibitors include phospholipid polymers, polyvinyl alcohol derivatives, phospholipid-polymer complexes, polyhydroxyethyl methacrylate, polyvinyl alcohol, agarose, chitosan, polyethylene glycol, albumin, and the like. These can be used in combination.

FIG. 3 shows a micrograph (×600) of the actually produced sphere culture member. In this sphere culture member, the openings and microholes are formed into squares, and their sides have a length of 150 μm and 10 μm, respectively.

Figure 4:
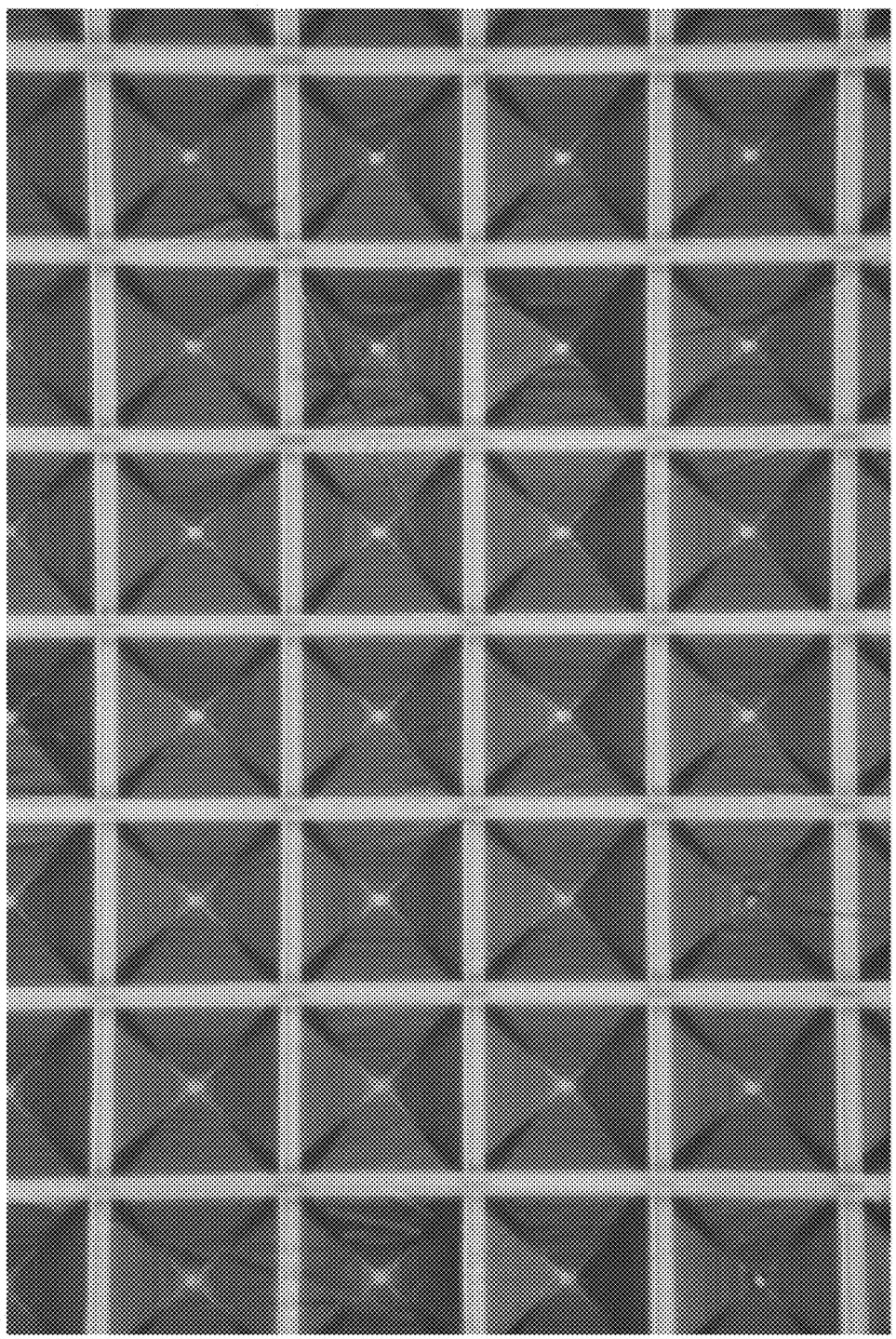
FIG. 4 is a micrograph obtained by photographing a state in which air bubbles are removed when a medium is dropped in the sphere culture member of the example.

The sphere culture member of the present embodiment makes it possible to suitably remove air bubbles through the microholes after dropping the medium. FIG. 4 is a micrograph obtained by photographing a state in which air bubbles are removed when a medium is dropped in the actually produced sphere culture member. The recesses of this sphere culture member look transparent, and it can be understood that no air bubbles are present. In this case, it was conformed that as a result of the movement of the medium dropped in the culture member on the wall surfaces of the recesses due to the capillary phenomenon, air bubbles present in the recesses were pushed from the microholes by the medium and immediately discharged.

Figure 5:
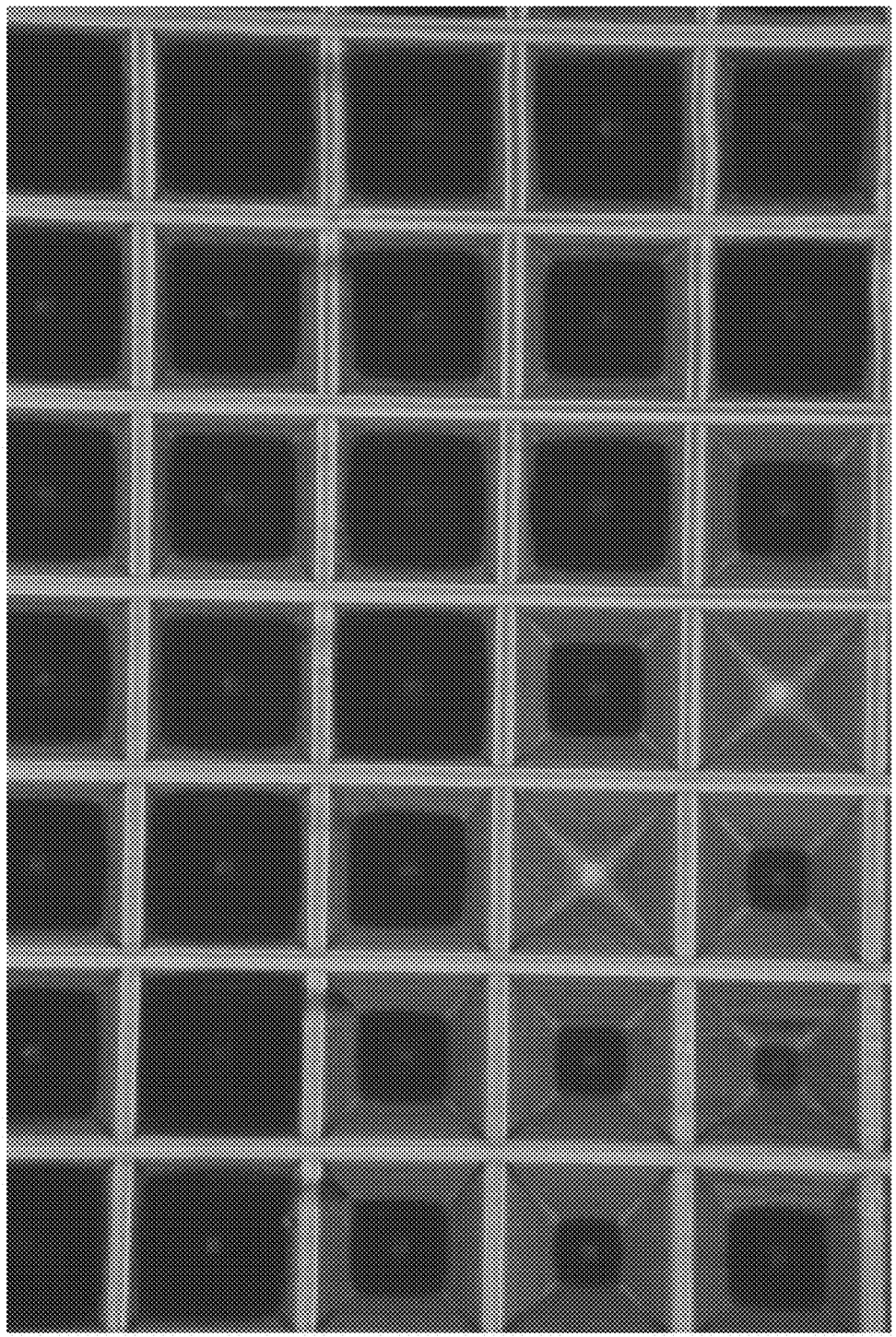
FIG. 5 is a micrograph obtained by photographing a state in which air bubbles remain when a medium is dropped in a culture member that has no microholes.

In contrast, FIG. 5 is a micrograph obtained by photographing a state in which air bubbles remain when a medium is dropped in a culture member that has no microholes. Thus, air bubbles look black in the recesses of the culture member that has no microholes, and it can be understood that air bubbles are present in the recesses.

Thus, according to the sphere culture member of the present embodiment, when a medium in which single cells are suspended is dropped in the step of forming spheres, air bubbles can be discharged from the microholes.

In contrast, in the case of a recess-processed member that has no microholes (the processed shape of the recesses is the same as that of the sphere culture container of the present embodiment, except that these recesses have no microholes), many air bubbles remain in the recesses when a medium is dropped. Thus, the sphere culture container of the present embodiment has an effect of discharging air bubbles due to the microholes.

Moreover, the sphere culture member of the present embodiment can be used to form a culture container, as descried later, and an air layer can be formed on the microhole side of the member.

That is, due to this air layer, the medium accommodated in the recesses can be maintained out of contact with the side walls (all of the walls that form the container) of the culture container. When single cells are seeded in the culture container in this state, even if the size of the microholes is larger than the size of the single cells, the surface tension of the medium does not allow the single cells and the medium to pass through the microholes, and the single cells are captured in the recesses. As a result, many single cells can be stacked in the recesses to suitably form spheres.

This culture method is similar to the so-called hanging-drop method; however, in the culture member of the present embodiment, the resulting spheres cannot pass through the microholes. On the other hand, with the hanging-drop method, spheres are formed in the medium layer supported in the air due to the surface tension of the medium projected from the holes. In contrast, in a culture container formed using the culture member of the present embodiment, spheres are formed on the surface of the recesses in the culture container. In this respect, the culture method performed using the culture member of the present embodiment is significantly different from the hanging-drop method.

Figure 6:
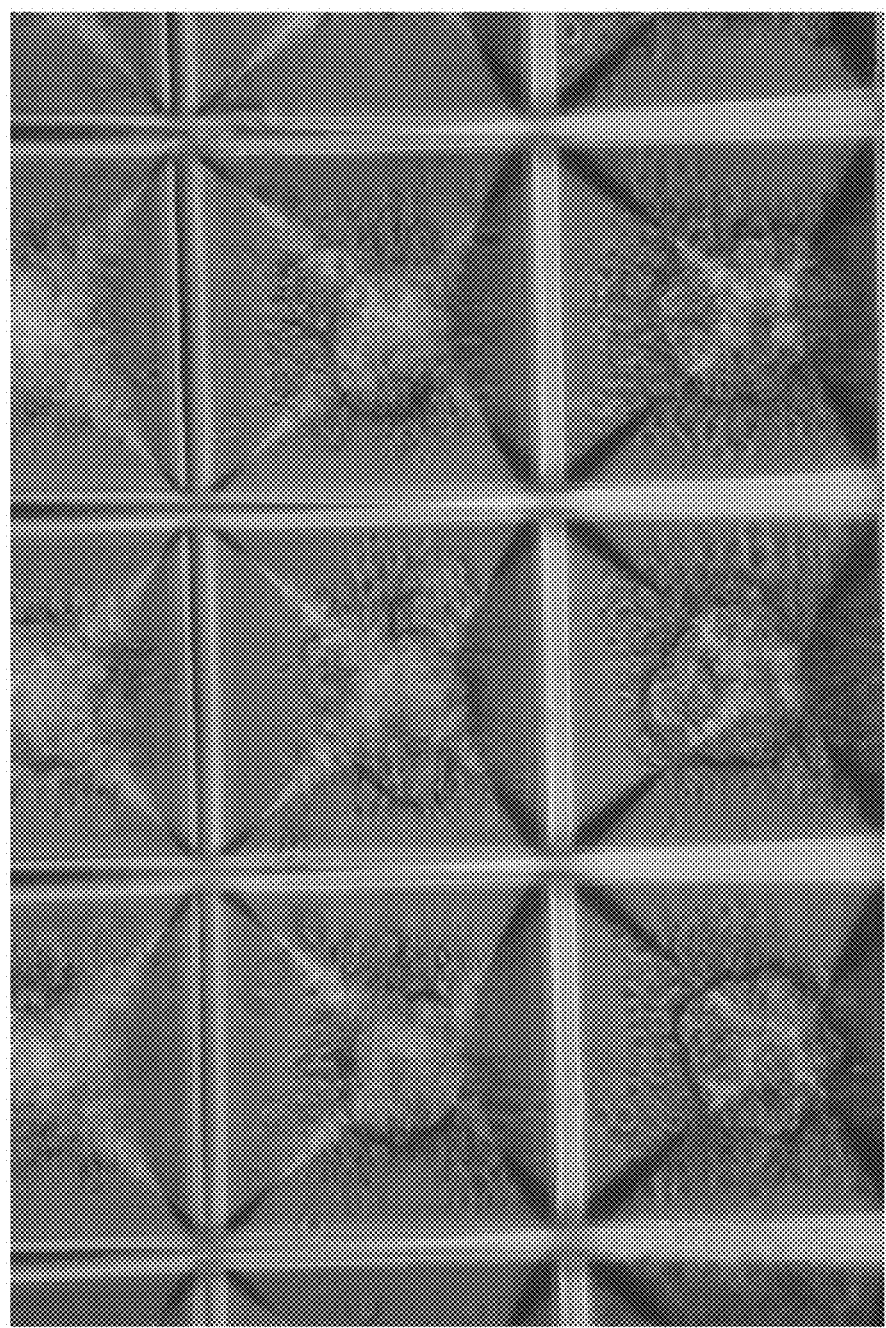
FIG. 6 is a micrograph obtained by photographing a state in which spheres are formed after single cells are seeded in a culture container formed using the sphere culture member of the example.

FIG. 6 is a micrograph obtained by photographing a state in which spheres are formed after single cells are dropped in a culture container formed using the actually produced sphere culture member. This is a state 24 hours after dropping single cells, and spheres are formed in all of the recesses. Further, many unnecessary single cells that cannot aggregate are stacked around the spheres.

Thus, the sphere culture member of the present embodiment makes it possible to form spheres without overlapping. Further, since the microholes are smaller than the size of spheres, the spheres are not discharged from the microholes, and the single cells can be discharged from the microholes.

Figure 7:
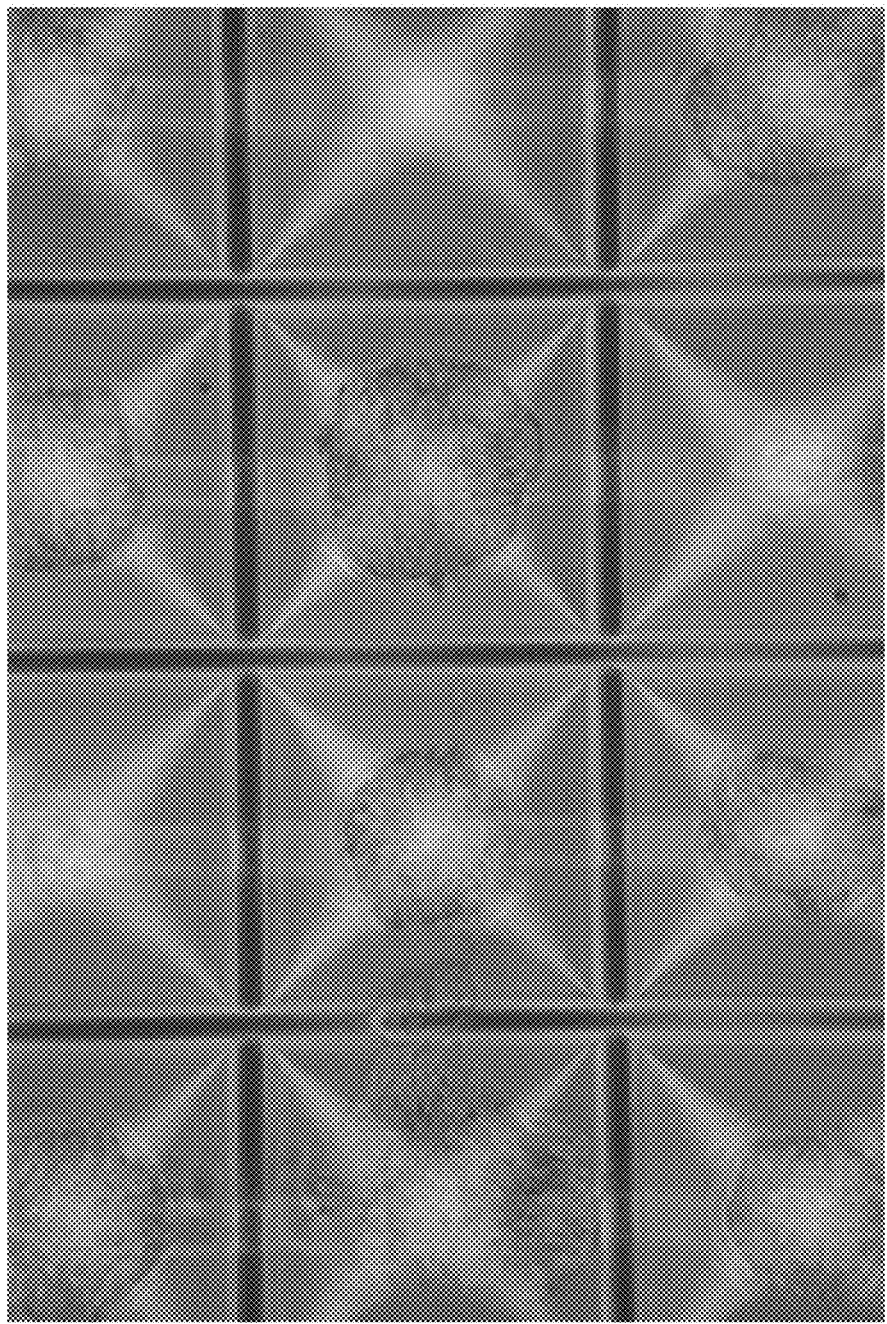
FIG. 7 is a micrograph obtained by photographing a state in which spheres are formed using a different culture container, the spheres are accommodated in the recesses of the sphere culture member of the example, and the medium is removed from the microholes.

Further, FIG. 7 is a micrograph obtained by photographing a state in which spheres are formed using a different culture container, the spheres are dropped in the actually produced sphere culture member, and the medium is removed from the microholes. Thus, the culture member of the present embodiment can also be used for the purpose of capturing spheres formed by using a different culture container to clean or count them.

Moreover, according to the sphere culture member of the present embodiment, the medium can be appropriately replaced while capturing, in the recesses, spheres formed by using this sphere culture member or spheres formed by using a different container. Therefore, it is possible to suitably perform sphere culture (e.g., differential induction).

Further, according to the sphere culture member of the present embodiment, a cleaning liquid can be rinsed while capturing the spheres in the recesses, and the spheres can be suitably cleaned.

Moreover, it is also possible to obtain spheres in a state of being arranged in sections each including a plurality of recesses, and to obtain such spheres with a uniform size depending on the recesses.

Furthermore, since it is possible to obtain spheres in a state of being arranged in each section, the spheres can be easily counted.

[Method for Processing Perforated Member]

Next, a method for processing a perforated member according to an embodiment of the present invention will be described with reference to FIGS. 8 to 13.

The method for processing a perforated member according to the present embodiment is a method for processing a perforated member to make a plurality of holes in the member using a mold; the member being a film having a first surface and a second surface on an opposite side of the first surface; the holes being recesses each having an opening in the first surface and one microhole for each opening in the second surface; in a two-dimensional model of the recesses viewed from a side surface, the mold and the film satisfying the formula: $t = a \times h / 2(a+b)$, wherein t is the thickness of the film, h is the height of projections in the mold corresponding to the recesses, b is the width of the tips of the projections in the mold corresponding to the microholes of the recesses, and a is the width between the tips of the adjacent projections in the mold; and the mold being pressed against the film to form the microholes in the film.

Figure 8:
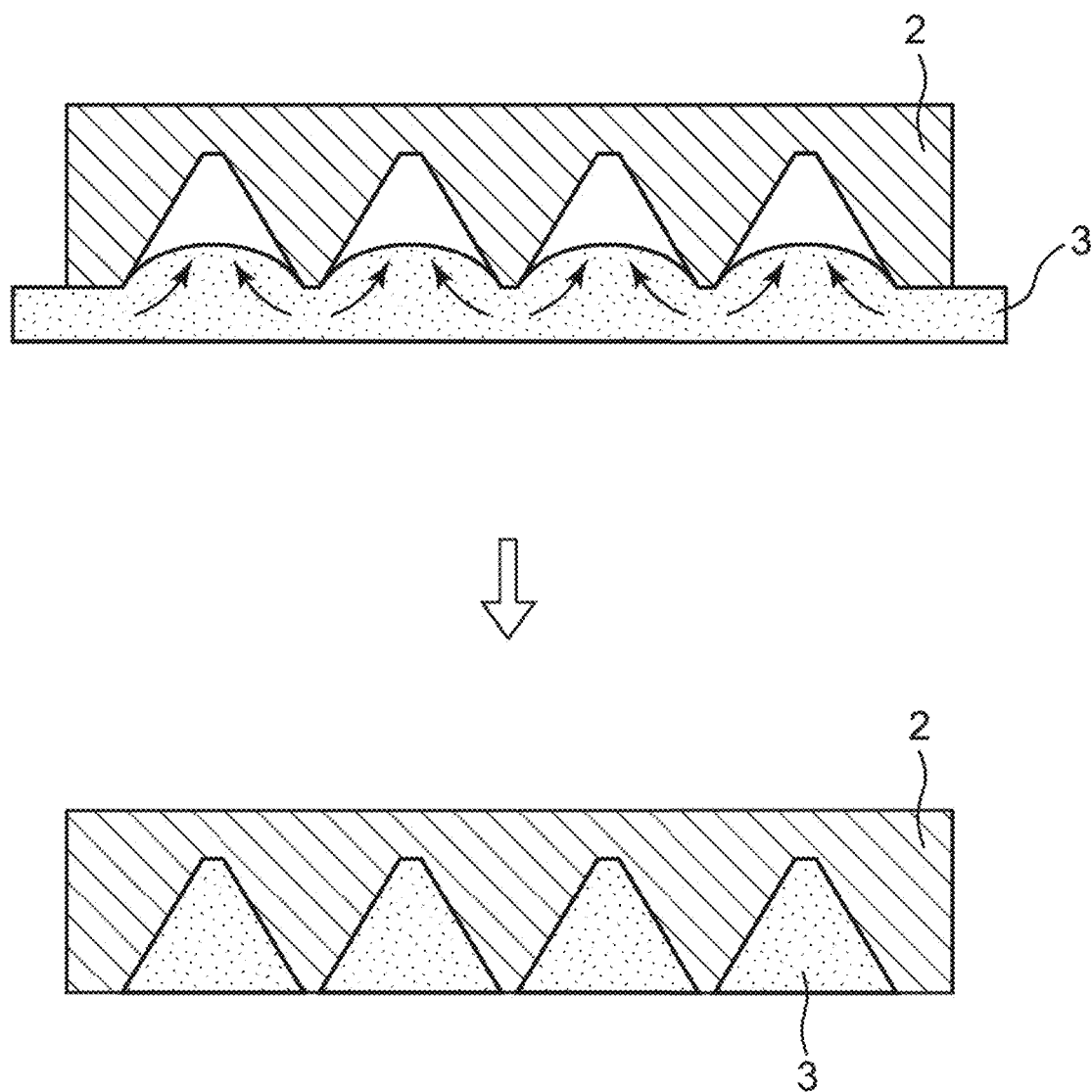
FIG. 8 is an explanatory diagram illustrating a state in which a processed resin material is poured into the recesses of a mold used in a method for processing a perforated member according to an embodiment of the present invention.

First, the history of developing the method for processing a perforated member according to the present embodiment will be described. FIG. 8 is an explanatory diagram illustrating a state in which a processed resin material 3 is poured into the recesses of a mold 2 used in the method for processing a perforated member according to the present embodiment. As shown in this figure, while the recesses of the mold 2 are filled with the processed resin material 3, microholes are formed in the layer of the processed resin material 3 by the projections of the mold 2, whereby the sphere culture member 1 of the present embodiment can be formed.

Then, when a material, a layer of which had a thickness smaller than the height of the recesses of the mold 2, was used as the processed resin material 3 to form a sphere culture member, microholes could not be easily formed even though the thickness of the layer was sufficiently smaller than the height of the recesses of the mold 2.

Moreover, when a material, a layer of which had a thickness much smaller than the height of the recesses of the mold 2, was used as the processed resin material 3, microholes could be formed; however, the recesses could not be sufficiently filled with the resin, thereby failing to appropriately form the side walls of the recesses.

That is, the method for processing a perforated member according to the present embodiment can be carried out by thermal imprinting (thermal transfer); however, it is necessary to make holes while appropriately adjusting the thickness of the processed resin material (film), and the size and depth of the mold. The processed resin material could not be penetrated simply by thermal transfer, thereby failing to appropriately form microholes.

In general processing of perforated members, such a problem does not usually occur. The reason for this is that, for example, when one through hole is formed in a member, the processed resin material corresponding to the hole can be easily removed and eliminated. Another reason for this is that when recesses are simply formed without penetration, the recesses can be easily formed, regardless of the thickness of the processed resin material.

However, it was not easy to form a sphere culture member having a number of recesses arranged at regular intervals, each recess having a microhole in its bottom surface, as in the sphere culture member of the present embodiment. For example, when an attempt was made to obtain a sphere culture member including a plurality of recesses each having a 10 μm microhole by using a mold having 150 μm projections to penetrate a film with a thickness of 100 μm, the film could not actually be penetrated, thereby failing to form microholes.

Here, as shown in FIG. 8, the processed resin material 3 located in the recesses of the sphere culture member escapes laterally to form peaks in the recesses of the mold as the mold 2 is pressed against it, thereby forming the side walls of the recesses of the sphere culture member. However, when the tips of the projections of the mold 2 do not penetrate the processed resin material 3 in a state where the processed resin material 3 has no space to escape and cannot move any further, this mold 2 cannot penetrate the processed resin material 3.

Then, the present inventors have succeeded in processing a sphere culture member including a plurality of arranged recesses each having a microhole by adjusting the volume of peaks formed in the recesses of the mold 2, the thickness of the layer of the processed resin material 3, and the interval of the projections in the mold 2.

Figure 9:
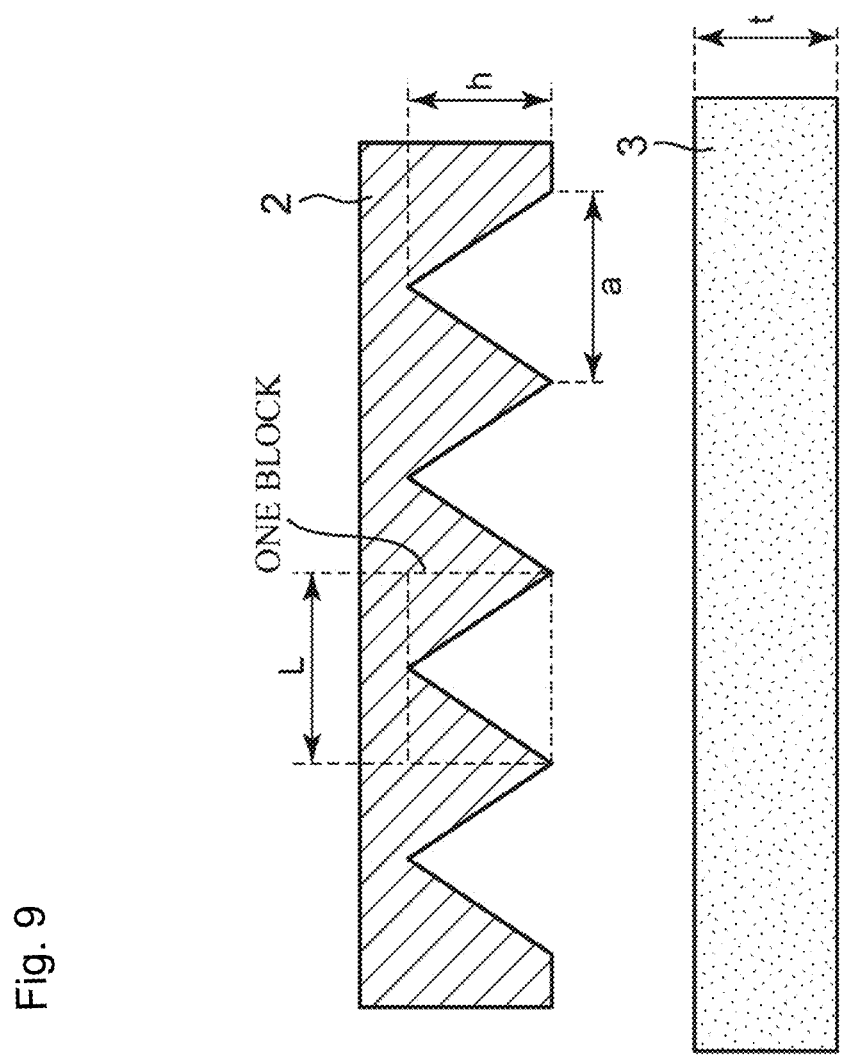
FIG. 9 is an explanatory diagram illustrating a case where the recesses and projections of a mold have the same volume in the method for processing a perforated member according to the embodiment of the present invention.

Next, the method for processing a perforated member according to the present embodiment will be described using a two-dimensional model to facilitate the understanding. FIG. 9 is an explanatory diagram illustrating a case where the recesses and projections of a mold have the same volume in the method for processing a perforated member according to the present embodiment.

As shown in this figure, one cycle of regularly arranged patterns is considered as one block, and the length of one block is taken as L.

In the range of one block, the processed resin material 3 pressed by the mold 2 continuously enters the recesses of the mold 2. In order for the tips of the projections of the mold to penetrate the processed resin material 3, it is necessary that the processed resin material 3 completely fills the recesses of the mold at the time of the penetration of the processed resin material 3.

That is, if the layer of the processed resin material 3 is too thick, the recesses of the mold 2 are filled with the resin, the mold 2 cannot be pressed any further against the processed resin material 3, and microholes cannot penetrate. In contrast, if the layer of the processed resin material 3 is too thin, microholes penetrate before the recesses of the mold 2 are filled with the resin. As a result, there is no more resin to enter the recesses of the mold 2, and the entire recesses cannot be filled, thereby failing to appropriately form the side walls of the recesses.

Therefore, in order for the mold 2 to penetrate the layer of the processed resin material 3 to form microholes, and for the recesses of the mold 2 to be filled with the processed resin material 3 to appropriately form the side walls of the recesses, it is necessary that the following formula is satisfied in the two-dimensional model.

Length L of one block×thickness t of processed resin material (film)=area of recess That is, as shown in FIG. 9, in the case where the recesses and projections of a mold 2 have the same volume, when the height of the projections in the mold 2 is h, and the width between the tips of the adjacent projections in the mold 2 is a, it is necessary to satisfy the formula: a×t=a×h/2. Therefore, the thickness t of the processed resin material is required to satisfy the following formula:

$$t = a \times h/2a = h/a$$

Accordingly, the use of a layer of a processed resin material 3 having a thickness that is half the height of the projections in the mold 2 makes it possible to realize the formation of through holes and the formation of side walls.

Figure 10:
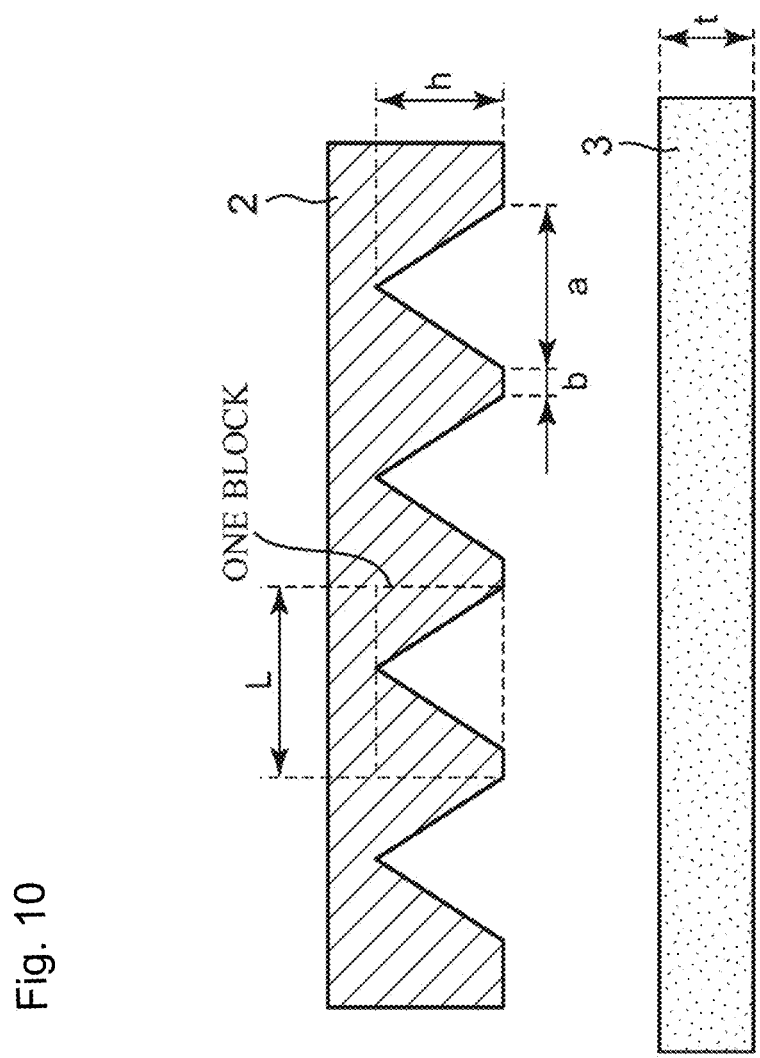
FIG. 10 is an explanatory diagram illustrating a case where the recesses and projections of a mold have different volumes in the method for processing a perforated member according to the embodiment of the present invention.

Similarly, as shown in FIG. 10, in the case where the recesses and projections of a mold 2 have different volumes, when the height of the projections in the mold 2 is h, the width of the tips of the projections in the mold 2 corresponding to the microholes is b, and the width between the tips of the adjacent projections in the mold 2 is a, it is necessary to satisfy the formula: (a+b)×t=a×h/2. Therefore, the thickness t of the processed resin material is required to satisfy the following formula:

$$t = a \times h/2(a+b)$$

That is, the use of a film of a processed resin material 3 having a thickness that satisfies this formula makes it possible to realize the formation of through holes and the formation of side walls.

Furthermore, although it is not shown, similarly in the case where the recesses and projections of a mold 2 have different volumes, when the height of the projections in the mold 2 is h, the width of the tips of the projections in the mold 2 corresponding to the microholes is b, the width between the tips of the adjacent projections in the mold 2 is a, and the width between the adjacent openings 11 in the first surface 1-1 of the sphere culture member 1 described above is c, it is necessary to satisfy the formula: $(a+b) \times t = (a+c) \times h/2$. Therefore, the thickness t of the processed resin material is required to satisfy the following formula:

$$t=(a+c) \times h/2(a+b)$$

That is, the use of a film of a processed resin material 3 having a thickness that satisfies this formula makes it possible to realize the formation of through holes and the formation of side walls.

In addition, in the present embodiment, it is preferable that the first surface 1-1 and the recesses 10 of the sphere culture member 1 are subjected to low-adhesion surface coating so that spheres and single cells do not adhere to the first surface 1-1 or the recesses 10. Specifically, it is preferable to apply a cell adhesion inhibitor (cell adhesion-reducing agent).

Accordingly, a cell adhesion inhibitor was applied to the surface of the layer of the processed resin material 3, and the mold 2 was then used to form through holes and side walls.

However, this method had a problem that the cell adhesion inhibitor was set off to the mold 2 and removed from the first surface 1-1 and the recesses 10 of the sphere culture member 1.

Therefore, before the method for processing a perforated member according to the present embodiment is performed, it is preferable to apply a cell adhesion inhibitor to the surface of the layer of the processed resin material 3 and also apply a mold release agent to the mold 2. Due to the use of the mold 2 thus coated with a mold release agent, the first surface 1-1 and the recesses 10 of the sphere culture member 1 can be suitably subjected to low-adhesion surface coating.

Figure 11:
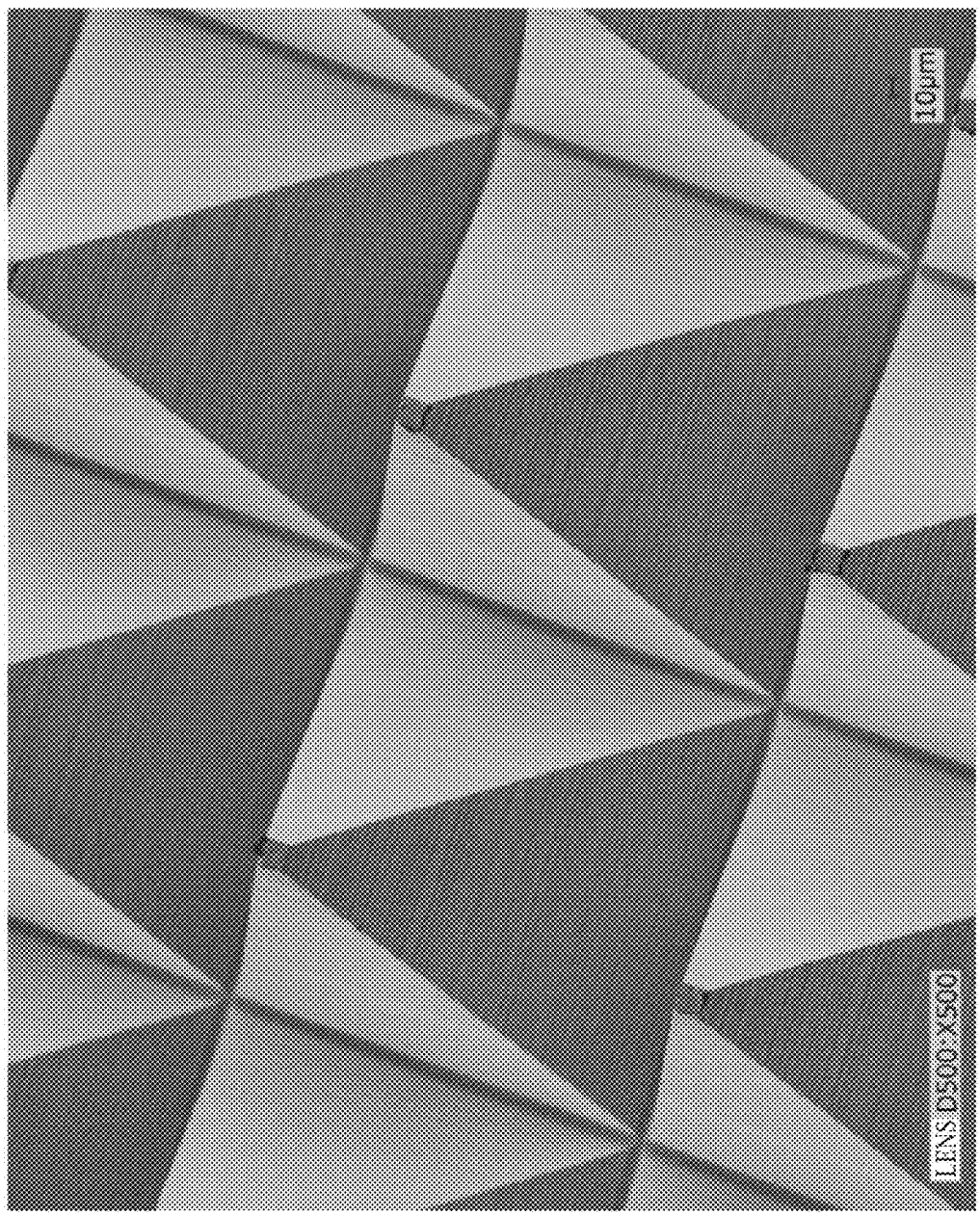
FIG. 11 is a micrograph obtained by photographing a mold that is produced to satisfy the formula in the method for processing a perforated member according to the embodiment of the present invention.

FIG. 11 shows a micrograph (×500) obtained by photographing a mold that satisfies the formula in the method for processing a perforated member according to the present embodiment. In addition, FIG. 12 shows a micrograph (×500) of a sphere culture member formed by using this mold.

Figure 12:
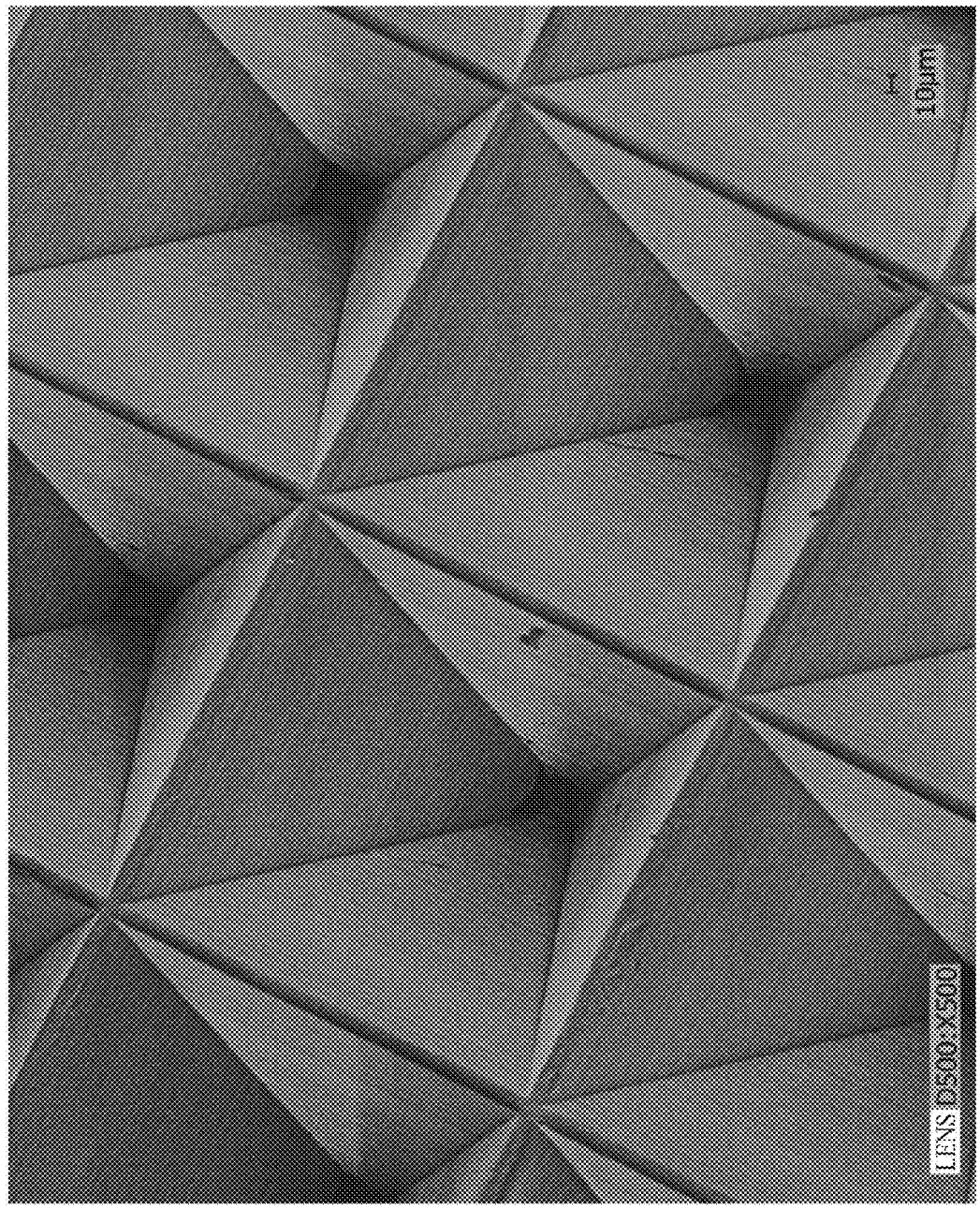
FIG. 12 is a micrograph obtained by photographing a sphere culture member of an example obtained using a mold that satisfies the formula in the method for processing a perforated member according to the embodiment of the present invention.

The method for processing a perforated member according to the present embodiment makes it possible to form a sphere culture member in which recesses each having a microhole are uniformly formed and the side walls of the recesses are also appropriately formed, as shown in FIG. 12.

Figure 13:
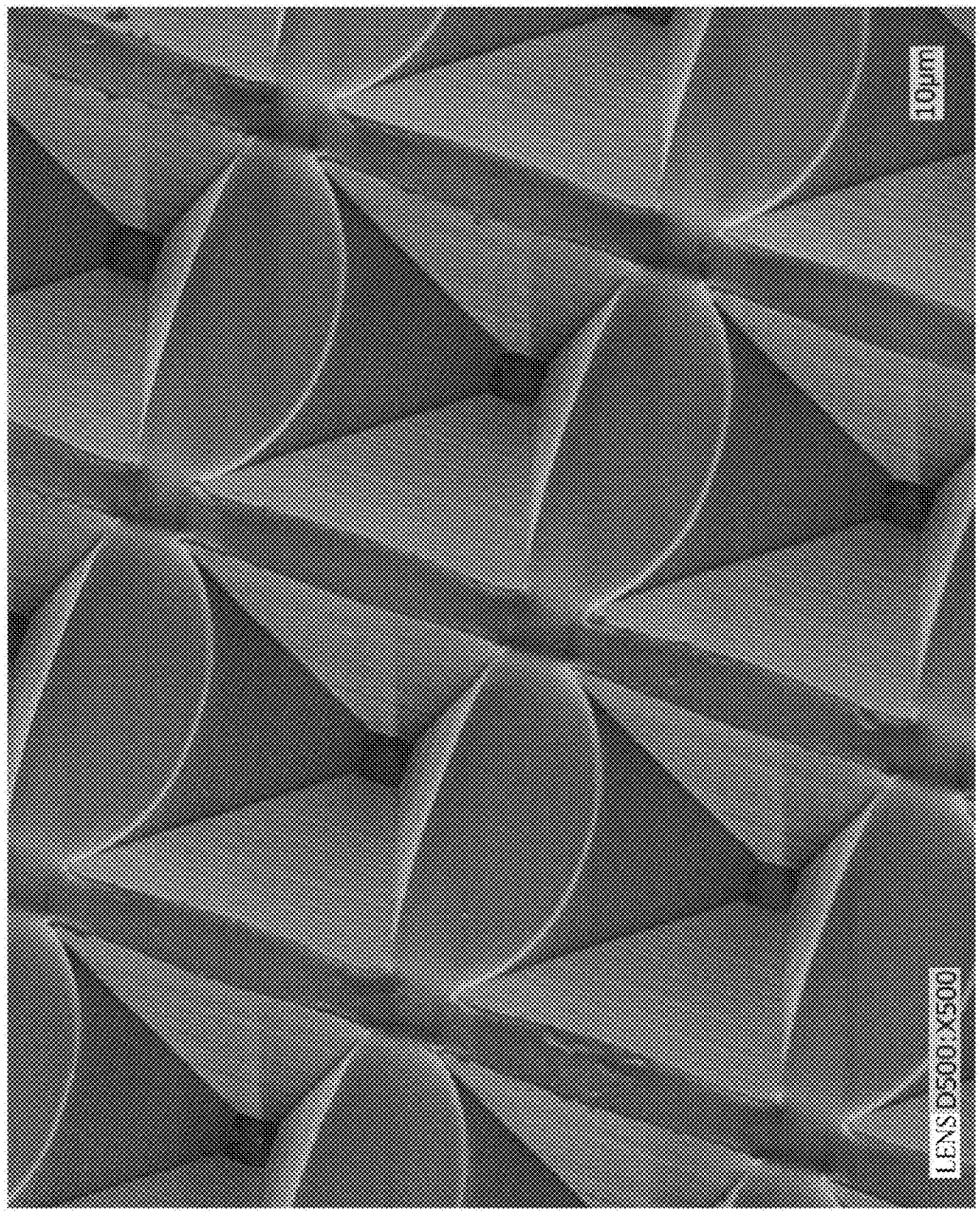
FIG. 13 is a micrograph obtained by photographing a member obtained using a mold that does not satisfy the formula in the method for processing a perforated member according to the embodiment of the present invention.

In contrast, FIG. 13 shows a micrograph (×500) obtained by photographing a member obtained by using a mold that does not satisfy the formula in the method for processing a perforated member according to the present embodiment. As shown in this figure, it is understood that, although microholes are formed in this sphere culture member, side walls are not sufficiently formed.

Thus, the method for processing a perforated member according to the present embodiment makes it possible to suitably form, for example, a sphere culture member including a plurality of recesses arranged at regular intervals and having microholes with a size of about 10 μm, using a processed resin material.

[Culture Container]

Next, the culture container according to an embodiment of the present invention will be described with reference to FIGS. 14 to 18.

The culture container of the present embodiment includes the first surface 1-1 of the sphere culture member 1 of the present embodiment described above as a culture surface.

Figure 14:
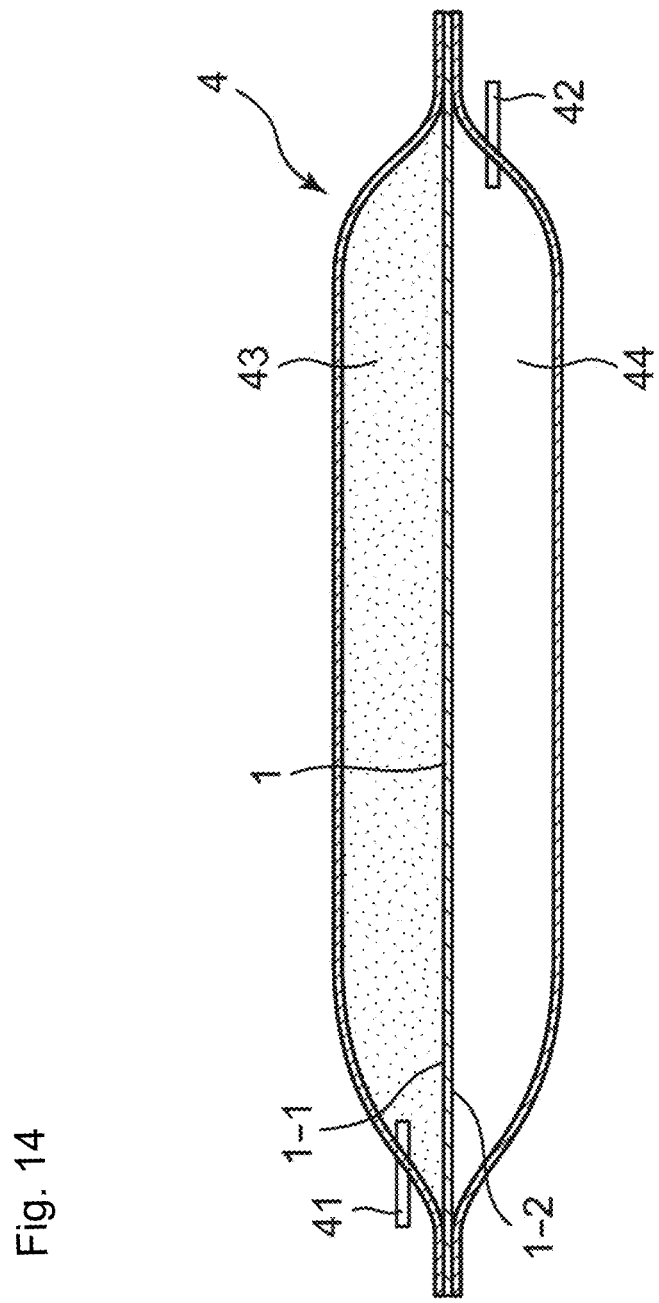
FIG. 14 is a schematic diagram illustrating a bag-shaped culture container (culture bag) that has the sphere culture member according to the embodiment of the present invention as a culture surface.

Specifically, as shown in FIG. 14, it is preferable that the culture container of the present embodiment is a culture bag 4 formed by sealing a flexible packaging material into a bag shape, the sphere culture member 1 separates the inside of the culture container into two spaces (a culture part 43 and an airtight part 44), and the respective two spaces are provided with ports (a port 41 on the culture part side and a port 42 on the airtight part side). The positions of these ports are not particularly limited; however, in order to facilitate liquid discharge, these ports are preferably arranged at diagonal positions, as shown in this figure.

This culture bag 4 makes it possible to fill the culture part 43 with a medium through the port 41, and to suitably form spheres in the sphere culture member 1.

The name of the airtight part is based on the fact that the airtight part is formed as a sealed space separate from the culture part in the culture container by filling the culture container of the present embodiment with a medium.

Here, the microholes 12 are formed in the recesses 10 of the sphere culture member 1. In general, the medium in the recesses 10 is supported by atmospheric pressure in the airtight part 44, and therefore the medium does not flow down from the microholes 12 to the airtight part 44 during sphere formation or sphere culture. On the other hand, to discharge the medium and the single cells from the microholes 12, the medium and the single cells can be easily discharged by sucking them from the airtight part 44, bringing the medium in the microholes 12 into contact with an absorber or the like, or filling the airtight part 44 with the medium to bring the microholes 12 into contact with the medium. The same applies to a culture container described later.

That is, a suction mechanism can be provided on the port 42 side, and the medium including the single cells etc. can be discharged from the airtight part 44 through the port 42. In this case, the medium can be discharged through the microholes 12 formed in the recesses of the sphere culture member, whereas the spheres cannot pass through the microholes 12 and are captured in the recesses.

Therefore, the culture container of the present embodiment makes it possible to appropriately replace the medium while capturing the spheres in the sphere culture member 1, and to appropriately culture and clean the spheres.

Further, the spheres obtained in this manner using the culture container of the present embodiment can be easily used because they have an almost uniform size and are arranged at regular intervals.

Moreover, it is also preferable that the culture container of the present embodiment is configured such that the culture container is made of a flexible packaging material sealed in a bag shape, the sphere culture member separates the inside of the culture container into two spaces to form a culture part and an airtight part, protrusion portions are provided in the culture container on an airtight part side wall facing the second surface of the sphere culture member in the airtight part on a rear side of the culture surface, and the protrusion portions of the airtight part side wall support regions of the second surface in which no microholes are disposed, thereby forming an air layer in the airtight part.

Furthermore, it is also preferable that the culture container of the present embodiment is configured such that the culture container is made of a flexible packaging material sealed in a bag shape, the sphere culture member separates the inside of the culture container into two spaces to form a culture part and an airtight part, the second surface of the sphere culture member is provided with protrusion portions, and the protrusion portions of the culture member are in contact with a side wall of the airtight part to form an air layer in the airtight part.

Figure 15:
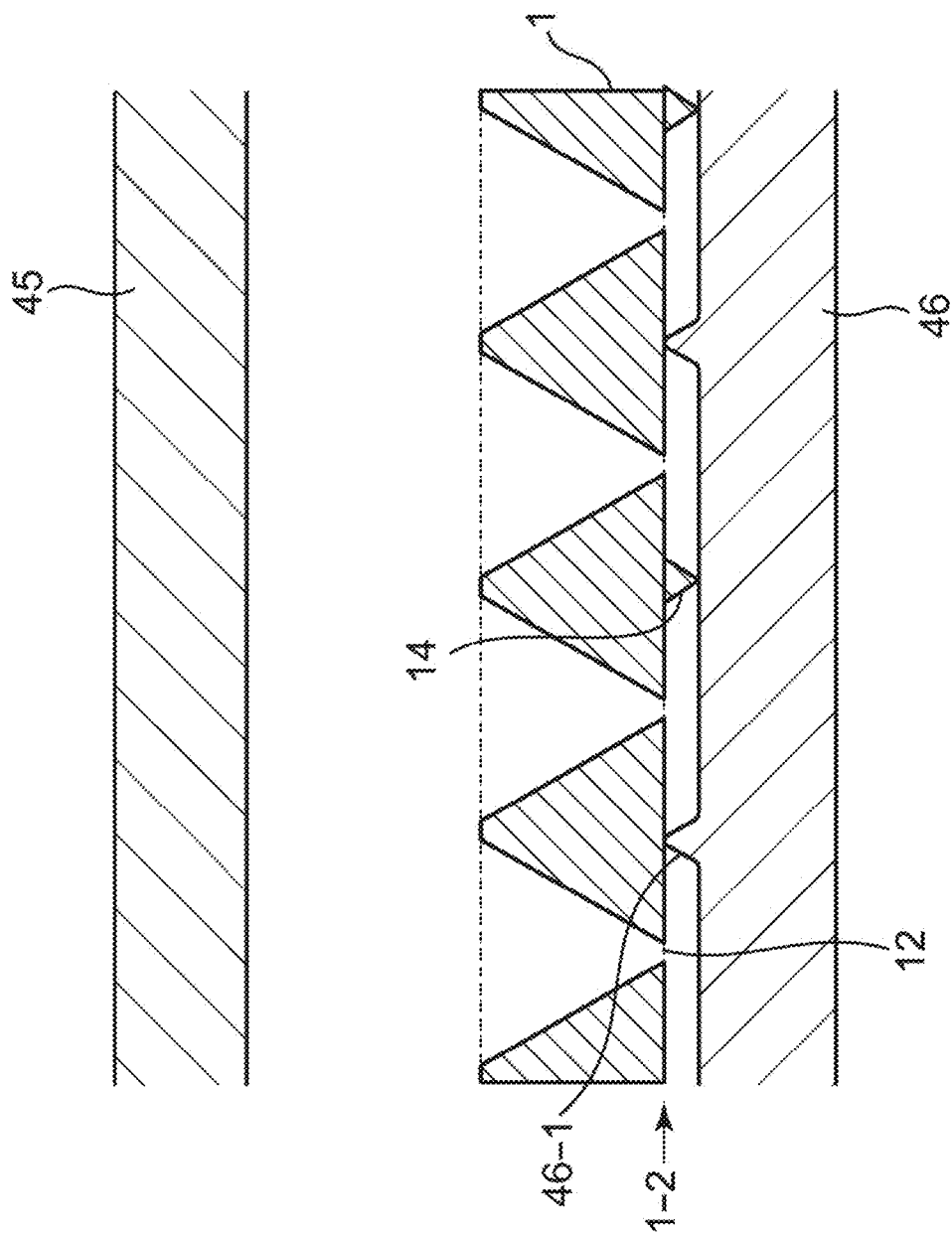
FIG. 15 is a schematic diagram illustrating a structure for forming an air layer in a bag-shaped culture container (culture bag) that has the sphere culture member according to the embodiment of the present invention as a culture surface.

FIG. 15 illustrates a structure for forming an air layer in the airtight part of the culture container of the present embodiment. This figure shows an enlarged state of a part of the sphere culture member viewed from a side surface.

That is, the airtight part side wall 46 is provided with protrusion portions (protrusion portions 46-1 of the airtight part side wall), and the protrusion portions 46-1 support regions of the second surface 1-2 in which no microholes 12 are disposed, thereby forming an air layer in the airtight part.

Moreover, the second surface 1-2 of the sphere culture member is provided with protrusion portions (protrusion portions 14 of the culture member), and the protrusion portions 14 of the culture member are in contact with the side wall of the airtight part, thereby forming an air layer in the airtight part.

Furthermore, it is also possible to provide either of the protrusion portions 46-1 of the airtight part side wall and the protrusion portions 14 of the culture member in the culture container of the present embodiment, thereby forming an air layer in the airtight part.

In addition, in the culture container of the present embodiment, the size and shape of the protrusion portions 46-1 of the airtight part side wall and the protrusion portions 14 of the culture member are not particularly limited. For example, their height can be set to 50 μm to 200 μm. Further, the interval and width of these protrusion portions are also not particularly limited, as long as the interval is not too wide to cause the member to bend. For example, these can be set to 2 mm to 3 mm.

Here, the reason why the protrusion portions 46-1 of the airtight part side wall support regions of the second surface 1-2 in which no microholes 12 are disposed is that if the protrusion portions 46-1 of the airtight part side wall are in contact with the medium through the microholes 12, the medium is flown into the airtight part due to the capillary phenomenon. Another reason for this is that before the formation of spheres, the single cells are also flown into the airtight part together with the medium.

Figure 16:
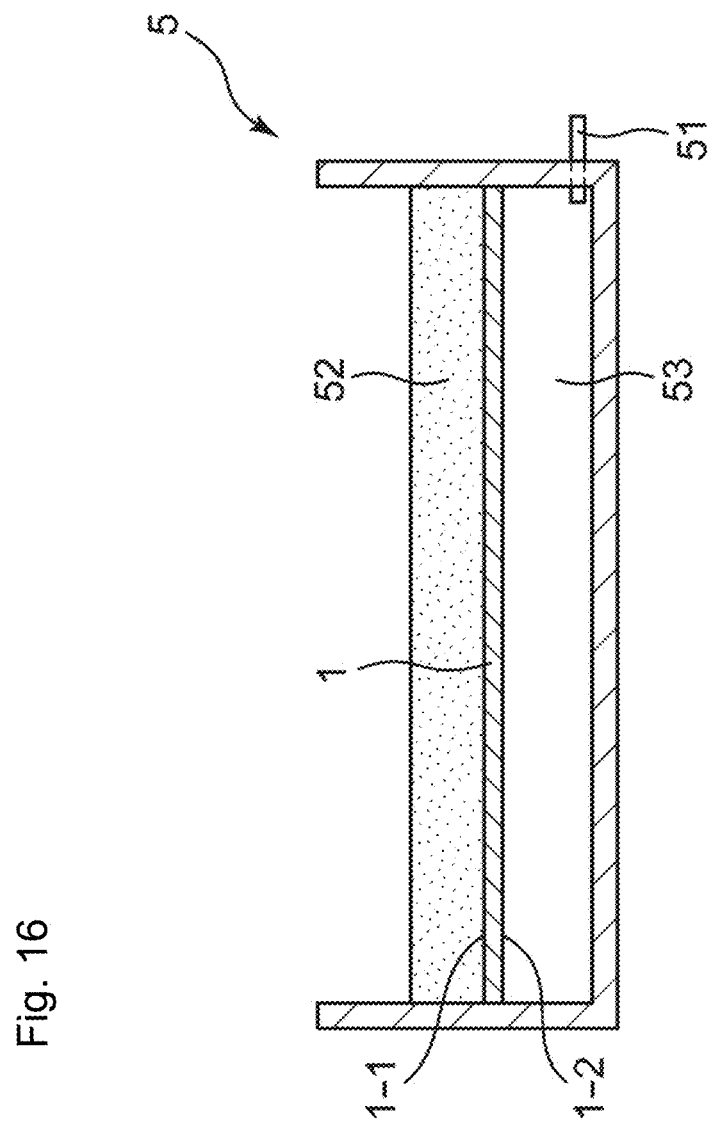
FIG. 16 is a schematic diagram illustrating a dish-shaped culture container (culture dish) that has the sphere culture member according to the embodiment of the present invention as a culture surface.

Further, as shown in FIG. 16, it is also preferable that the culture container of the present embodiment is a culture dish 5 formed into a dish shape, a closed space (an airtight part 53) is formed by the sphere culture member 1 in the culture container, and the second surface 1-2 of the sphere culture member 1 is disposed in the closed space. Further, it is also preferable that a port 51 is provided in the culture dish 5 on the closed space side.

The culture dish 5 makes it possible to fill the culture part 52 with a medium, and to suitably form spheres in the sphere culture member 1.

In addition, a suction mechanism can be provided on the port 51 side to discharge the medium including the single cells etc. from the airtight part 53 through the port 51. Therefore, while capturing the spheres in the sphere culture member 1, it is possible to appropriately replace the medium and suitably culture and clean the spheres.

Further, the spheres obtained in this manner using the culture container of the present embodiment can be easily used because they have an almost uniform size and are arranged at regular intervals.

Figure 17:
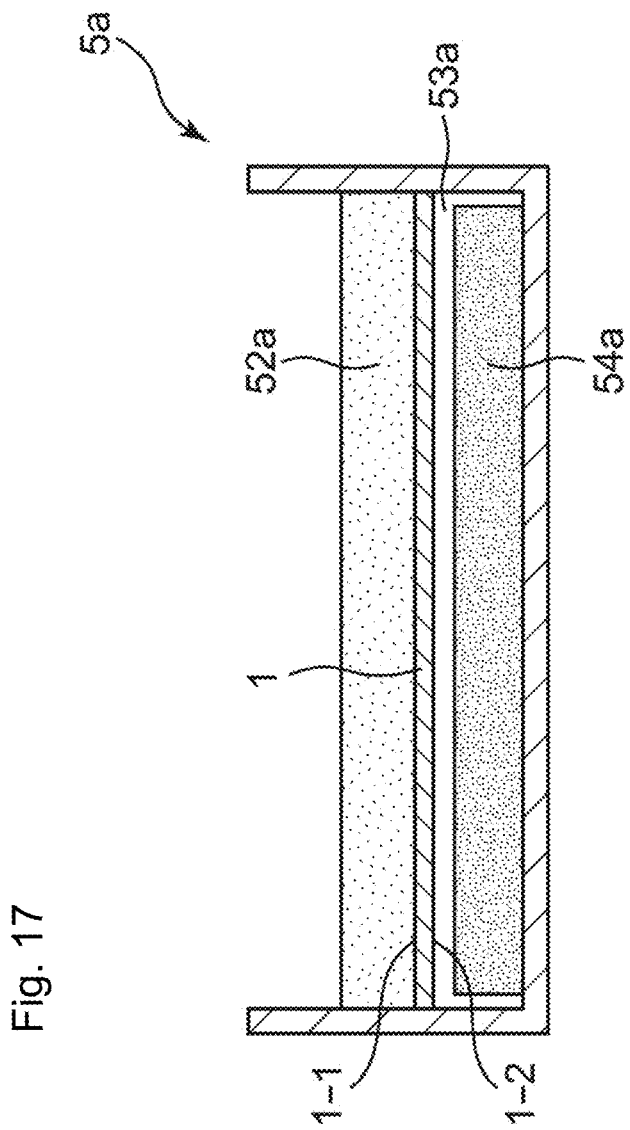
FIG. 17 is a schematic diagram illustrating a dish-shaped culture container that has the sphere culture member according to the embodiment of the present invention as a culture surface, and that also has an absorber provided therein.

Moreover, as shown in FIG. 17, it is also preferable that the culture container of the present embodiment is a culture dish 5a including a suction mechanism or an absorber 54a on the closed space (airtight part 53a) side in which the second surface 1-2 of the sphere culture member 1 is disposed.

When the culture container of the present embodiment has such a structure, the medium including the single cells etc. can be discharged from the culture part 52a by the suction mechanism or the absorber 54a. In this case, the medium can be discharged through the microholes 12 formed in the recesses of the sphere culture member, whereas the spheres cannot pass through the microholes 12 and are captured in the recesses. Therefore, while capturing the spheres in the sphere culture member 1, it is possible to appropriately replace the medium and suitably culture and clean the spheres.

Figure 18:
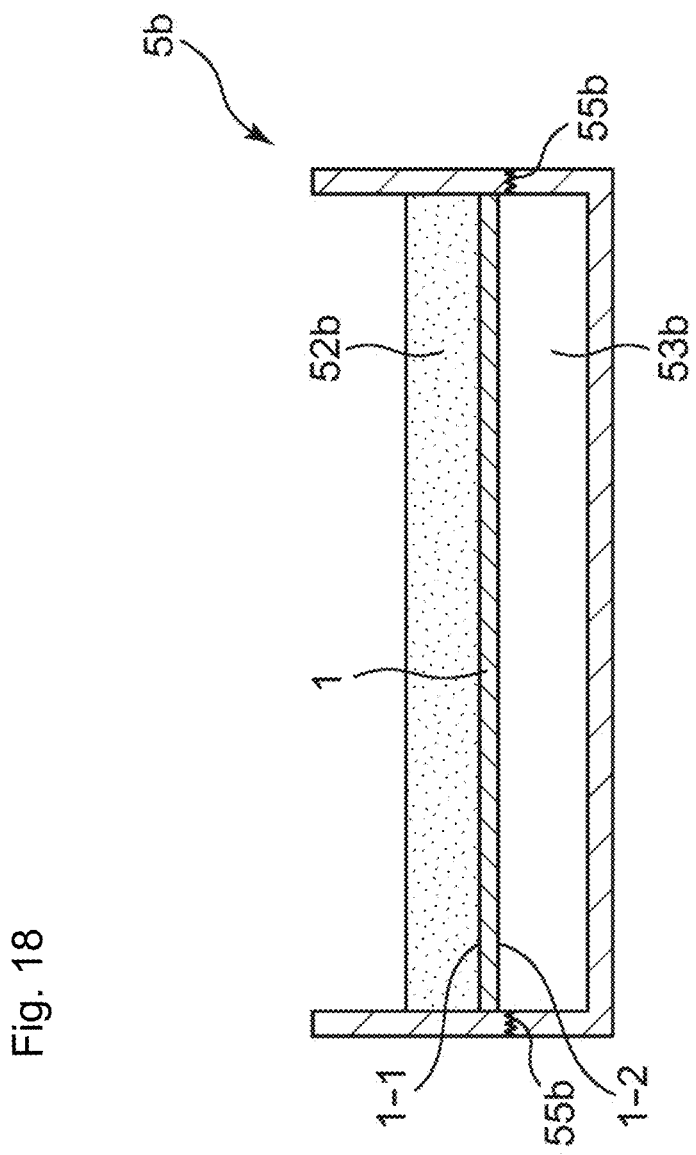
FIG. 18 is a schematic diagram illustrating a dish-shaped culture container that has the sphere culture member according to the embodiment of the present invention as a culture surface, and that also has an easy-to-cut portion in its side wall.

Further, as shown in FIG. 18, it is also preferable that the culture container of the present embodiment is a culture dish 5b including an easy-to-cut portion 55b in a side wall on the closed space (airtight part 53b) side. The easy-to-cut portion 55b is formed, for example, by making the side wall on the airtight part 53b side into a mating type to keep the airtightness of the airtight part 53b, and can make the side wall separable.

When the culture container of the present embodiment has such a structure, after the culture of spheres is completed, the culture dish 5b can be easily cut at the easy-to-cut portion 55b, and the sphere culture member in which the formed spheres are accommodated can be easily detached.

The structures shown in FIGS. 16 to 18 can be combined to produce the culture container of the present embodiment.

When a culture bag is produced as the culture container of the present embodiment, examples of the material thereof include polyethylene, ethylene-α-olefin copolymers, cyclic olefin copolymers, ethylene-vinyl acetate copolymers, ionomers, ionomers using ethylene-acrylic acid or -methacrylic acid copolymers and metal ions, and the like. Other usable examples include polyolefins, styrene-based elastomers, polyester-based thermoplastic elastomers, silicone-based thermoplastic elastomers, silicone resins, and the like. Further, it is preferable to use a polyurethane-based thermoplastic elastomer, a polyester-based thermoplastic elastomer, a silicone-based thermoplastic elastomer, a styrene-based elastomer, a fluorine-based resin, or a combination thereof; and it is particularly preferable to use a polyethylene-based resin.

Moreover, when a culture dish is produced as the culture container of the present embodiment, the same materials as those for the sphere culture member 1 described above can be used.

Further, the culture container of the present embodiment can be suitably used as a cleaning container for cleaning spheres, tissues, etc.

That is, according to the cleaning container of the present embodiment, while capturing the spheres etc. in the recesses, PBS (phosphate buffered saline) or the like can be rinsed and discharged through the microholes. Therefore, it is possible to easily clean the spheres etc.

Next, the applications of the culture container of the present embodiment will be described in detail.

First, the culture container of the present embodiment can be suitably used for the formation of spheres, as described above. That is, when single cells are seeded in the recesses of the sphere culture member provided in the culture container, the cells roll down the inclined surfaces of the recesses 10 to be unified into one and aggregate, thereby forming spheres.

When using a conventional microwell plate, spheres could be formed; however, there was a problem that single cells that were not used for sphere formation could not be removed. Further, it was difficult to, for example, appropriately replace the medium.

Moreover, there is a method for forming spheres by placing single cells in a bioreactor, and rotating the bioreactor so that the cells gradually aggregate. However, this method had a problem that it was difficult to ensure the uniformity of spheres, resulting in a low yield.

In addition, the culture container of the present embodiment can be suitably used for sphere culture. That is, after the formation of spheres, differentiation can be induced in the sphere state. The culture container of the present embodiment makes it possible to replace the medium and completely exchange differentiation-inducing factors through the microholes provided in the bottom surface of the recesses of the sphere culture member.

When using a conventional microwell plate, the spheres were stirred up during replacement of the medium or exchange of differentiation-inducing factors, which often caused defects.

In addition, bioreactors had a problem of low exchange efficiency, although the replacement of the medium and the exchange of differentiation-inducing factors were possible.

Further, the culture container of the present embodiment can be suitably used for sphere cleaning. That is, according to the culture container of the present embodiment, the spheres can be cleaned with a saline solution or the like, and the cleaning liquid can be discharged through the microholes provided in the bottom surface of the recesses of the sphere culture member. In this case, the spheres do not overlap each other, and all of the spheres can be allowed to pass under uniform conditions.

Moreover, the culture container of the present embodiment can be suitably used for sphere arrangement. That is, for example, when spheres are administered by subcutaneous implant or the like, it is preferable to immobilize the spheres on a gel or the like. According to the culture container of the present embodiment, spheres can be obtained in a state of being arranged at regular intervals, and a gel can be injected thereinto, whereby solidification or transfer to the gel can be easily performed.

Furthermore, the culture container of the present embodiment can be suitably used to arrange the spheres, and thus can be suitably used to count the spheres.

EXAMPLES

Hereinafter, examples of the sphere culture member, the culture container, and the method for processing a perforated member according to embodiments of the present invention will be described.

First, a sphere culture member was produced using the method for processing a perforated member according to the present embodiment.

Specifically, a male mold in which truncated square pyramid projections were arranged was produced by treating silicon. In this case, one side of the bottom surface of each truncated square pyramid had a length of 150 μm, and one side of the upper surface of the truncated square pyramid had a length of 10 μm. Moreover, the mold was formed into a 3 cm×3 cm square, and about 35,000 of projections were formed therein. Further, the entire surface of the mold was coated with a mold release agent. FIG. 8 is a micrograph of the mold obtained in this manner.

Next, this mold was pressed against polyethylene, which was a processed resin material, to thereby produce the sphere culture member of the present embodiment. Prior to this operation, the polyethylene surface was coated with a phospholipid polymer ethanol solution as a cell adhesion inhibitor.

In this case, when the height of the projections in the mold was h, the width of the tips of the projections in the mold was b, and the width between the tips of the adjacent projections in the mold was a, a was 196 μm, b was 10 μm, and h was 210 μm. In order to appropriately form a sphere culture member, it is necessary that the thickness t of polyethylene satisfies the formula $t=h \times a/2(a+b)$ mentioned above.

Therefore, it is necessary to set the thickness t of polyethylene to $210 \times 196/2(196+10) \approx 99.9$ μm. Because the thickness of polyethylene was set as described above, microholes could suitably penetrate in the sphere culture member, and the side walls of the recesses could be suitably formed. FIG. 12 is a micrograph of the sphere culture member produced in this manner.

Next, a culture dish using this sphere culture member as a culture surface was prepared. Then, iPS cells (strain 1231A3) were used to form spheres. The number of cells seeded was about $1.0 \times 10^7$ cells. Further, as the medium, StemFit AK02N (item number: RCAK02N, AJINOMOTO Co., Inc.) was used.

Specifically, the above medium containing 10 mM Y-27632 (Wako Pure Chemical Industries, Ltd.) was poured into the culture dish, and a cell suspension containing the iPS cells was poured and allowed to stand overnight.

FIG. 6 is a micrograph of the spheres obtained in this manner. As shown in this figure, the spheres with an almost uniform size are arranged at regular intervals in the recesses of the sphere culture member.

As explained above, the sphere culture member, the culture container, the method for processing a perforated member, and the cleaning container according to embodiments of the present invention make it possible to efficiently exchange the medium, clean spheres, and arrange spheres at regular intervals in the formation of spheres. In this case, due to the use of the sphere culture member according to the present embodiment, these operations can be carried out with one member without using other members.

It is also possible to preferably form a member including a plurality of recesses arranged at regular intervals and having microholes with a size of about 10 μm, using a processed resin material.

The present invention is not limited to the above-mentioned embodiments and examples, and it is needless to say that various modifications are possible within the scope of the present invention.

For example, the size of the sphere culture member is not limited to the size of the example, and can be suitably changed to a size that can form, for example, 500,000 to a million of spheres.

INDUSTRIAL APPLICABILITY

The present invention can be suitably used, for example, for efficiently mass-producing spheres with a uniform size arranged at regular intervals.

The documents described in the specification and the Japanese patent application claiming the priority under the Paris Convention to the invention are incorporated herein by reference in its entirety.

DESCRIPTION OF REFERENCE SIGNS

1: Sphere culture member
1-1: First surface
1-2: Second surface
10: Recess
11: Opening
12: Microhole
13: Wall surface 14: Protrusion portion of culture member
2: Mold
3: Processed resin material (film)
4: Culture bag
41: Port (culture part side)
42: Port (airtight part side)
43: Culture part
44: Airtight part
45: Culture part side wall
46: Airtight part side wall
46-1: Protrusion portion of airtight part side wall
5, 5*a*, 5*b*: Culture dish
51: Port
52, 52*a*, 52*b*: Culture part
53, 53*a*, 53*b*: Airtight part
54*a*: Absorber
55*b*: Easy-to-cut portion

The invention claimed is:

1. A culture container, which is one culture bag, the one culture bag comprising:
    two side walls;
    a sphere culture member comprising a film, the sphere culture member being disposed between the two side walls such that a three-layered structure is formed by the two side walls and the sphere culture member, wherein:
    the sphere culture member captures spheres and separates an inside of the container into two spaces between the two side walls;
    the sphere culture member has a first surface, a second surface facing away from the first surface, and a plurality of recesses;
    in the first surface, a plurality of openings are formed in and corresponding to the plurality of the recesses, respectively;
    a plurality of microholes are formed in the second surface, and each of the plurality of microholes communicates with one of the plurality of the openings in the first surface;
    a wall surface of the each of the plurality of the recesses is inclined from a corresponding one of the plurality of the openings toward a microhole of the plurality of microholes; and
    a circle or inscribed circle of each of the plurality of the openings has a diameter a of 50 μm or more and 1 mm or less, a circle or inscribed circle of each of the plurality of microholes has a diameter b of 1 μm or more and less than 200 μm, and a and b satisfy a>b.

2. The culture container according to claim 1, wherein the culture container is formed of a flexible material, and each of the two spaces is provided with a port.

3. The culture container according to claim 1, wherein
    the culture container is formed of a flexible material,
    the two spaces form a culture part and an airtight part,
    the airtight part is formed as a space, in entirety, sealed by filling the culture container with a medium such that the medium seals the each of the plurality of the openings,
    protrusion portions are provided in the culture container on a bottom wall of the airtight part facing the second surface of the sphere culture member in the airtight part on a culture surface, and the protrusion portions of the airtight part bottom wall support regions of the second surface in which no microholes are disposed, thereby forming an air layer in the airtight part.

4. The culture container according to claim 1, wherein
    the culture container is formed of a flexible material,
    the two spaces form a culture part and an airtight part,
    the airtight part is formed as a space, in entirety, sealed by filling the culture container with a medium such that the medium seals the each of the openings,
    the second surface of the sphere culture member is provided with protrusion portions, and
    the protrusion portions of the culture member are in contact with a bottom wall of the airtight part to form an air layer in the airtight part.

* * * * *